US010368931B2

(12) United States Patent
Honma et al.

(10) Patent No.: US 10,368,931 B2
(45) Date of Patent: Aug. 6, 2019

(54) SPACER, IMPLANT ASSEMBLY INCLUDING THE SAME, MANUFACTURING METHOD OF SPACER, AND SURGICAL METHOD FOR SPACER INDWELLING

(71) Applicant: TERUMO KABUSHIKI KAISHA, Tokyo (JP)

(72) Inventors: Yasuyuki Honma, Kanagawa (JP); Makoto Narita, Hadano (JP)

(73) Assignee: TERUMO KABUSHIKI KAISHA, Shibuya-Ku, Tokyo (JP)

(*) Notice: Subject to any disclaimer, the term of this patent is extended or adjusted under 35 U.S.C. 154(b) by 807 days.

(21) Appl. No.: 14/872,567

(22) Filed: Oct. 1, 2015

(65) Prior Publication Data

US 2016/0022344 A1 Jan. 28, 2016

Related U.S. Application Data

(63) Continuation of application No. PCT/JP2013/059938, filed on Apr. 1, 2013.

(51) Int. Cl.
*A61B 17/88* (2006.01)
*A61F 2/44* (2006.01)
(Continued)

(52) U.S. Cl.
CPC ........ *A61B 17/8855* (2013.01); *A61B 17/562* (2013.01); *A61B 17/7065* (2013.01); *A61F 2/44* (2013.01); *A61F 2/441* (2013.01); *A61F 2/4611* (2013.01); *A61M 29/02* (2013.01); *A61B 2017/00557* (2013.01); *A61F 2/4405* (2013.01);
(Continued)

(58) Field of Classification Search
CPC .................. A61F 2/441; A61F 2/4611; A61M 2025/1045; A61M 2025/1061; A61M 2025/1086; A61M 25/1011; A61M 2025/1013; A61M 2025/1015;
(Continued)

(56) References Cited

U.S. PATENT DOCUMENTS 5,209,728 A * 5/1993 Kraus ................. A61M 25/104
604/913
5,556,413 A * 9/1996 Lam .......................... A61F 2/88
606/198

(Continued)

FOREIGN PATENT DOCUMENTS

JP 10-234873 A 9/1998
JP 2011-125621 A 6/2011

OTHER PUBLICATIONS

International Search Report (PCT/ISA/210) dated Jun. 11, 2013, by the Japanese Patent Office as the International Searching Authority for International Application No. PCT/JP2013/059938.

*Primary Examiner* — Anu Ramana
(74) *Attorney, Agent, or Firm* — Buchanan Ingersoll & Rooney PC

(57) ABSTRACT

A spacer and implant assembly are disclosed, the spacer including an outer balloon that is folded so as to be dilatable, and an inner balloon that is folded so as to be dilatable, and that is removably inserted into the outer balloon. The inner balloon dilates in response to introduction of a dilating fluid having a lower viscosity than a viscosity of a filling material inserted into the outer balloon, and the outer balloon dilates in response to the dilation of the inner balloon.

19 Claims, 17 Drawing Sheets

(51) Int. Cl.
- *A61F 2/46* (2006.01)
- *A61B 17/70* (2006.01)
- *A61B 17/56* (2006.01)
- *A61M 29/02* (2006.01)
- *A61F 2/30* (2006.01)
- *A61B 17/00* (2006.01)

(52) U.S. Cl.
CPC ............. *A61F 2002/3013* (2013.01); *A61F 2002/30171* (2013.01); *A61F 2002/30583* (2013.01); *A61F 2002/30586* (2013.01)

(58) Field of Classification Search
CPC ....... A61M 2025/1004; A61B 17/7097; A61B 17/8855; A61B 17/8858
See application file for complete search history.

(56) References Cited

U.S. PATENT DOCUMENTS

| | | | |
|---|---|---|---|
| 5,879,282 A | | 3/1999 | Fischell et al. |
| 6,471,672 B1 * | | 10/2002 | Brown .................... A61F 2/958 604/101.01 |
| 2005/0177130 A1 * | | 8/2005 | Konstantino ......... A61M 25/10 604/509 |
| 2009/0118833 A1 | | 3/2009 | Hudgins |

* cited by examiner

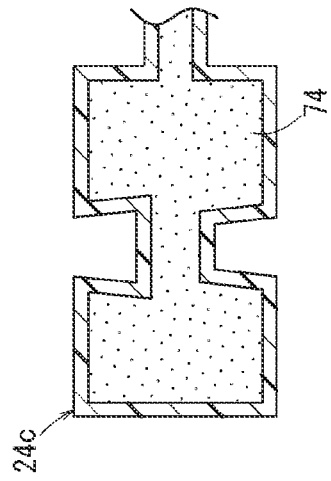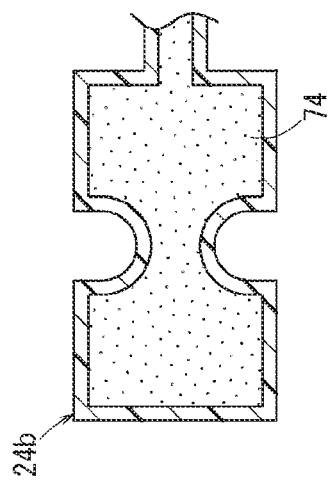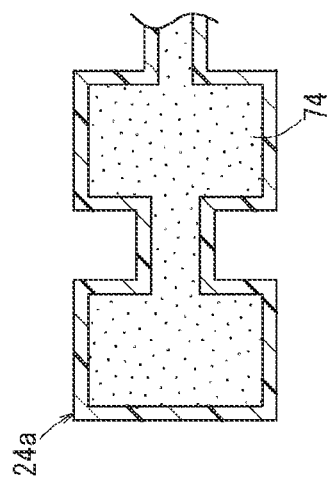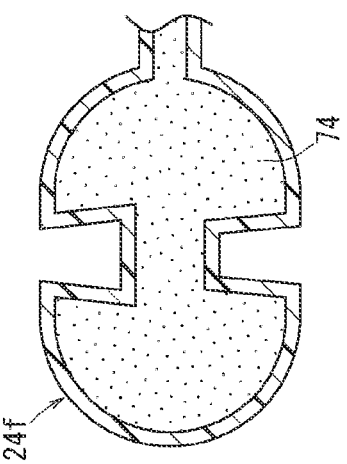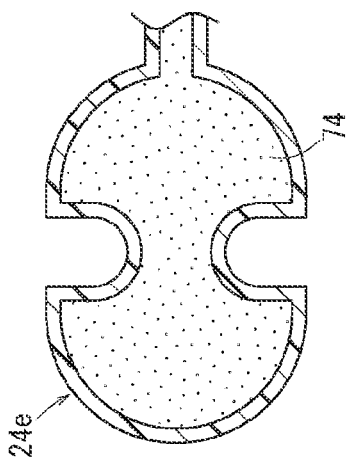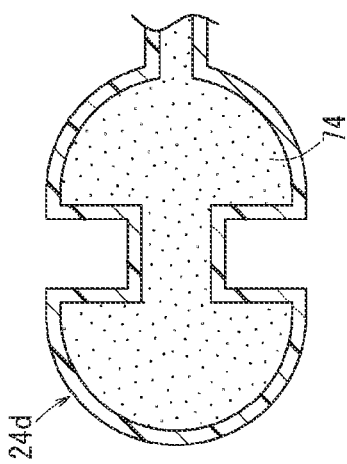

SPACER, IMPLANT ASSEMBLY INCLUDING THE SAME, MANUFACTURING METHOD OF SPACER, AND SURGICAL METHOD FOR SPACER INDWELLING

CROSS-REFERENCES TO RELATED APPLICATIONS

This application is a continuation of International Application No. PCT/JP2013/059938 filed on Apr. 1, 2013, the entire content of which is incorporated herein by reference.

TECHNICAL FIELD

The present disclosure generally relates to a spacer which indwells between bones so as to expand a space between the bones, an implant assembly including a spacer, a manufacturing method of a spacer, and a surgical method for spacer indwelling.

BACKGROUND DISCUSSION

Lumbar spinal canal stenosis is a disease in which the spinal canal is stenosed due to recession degeneration of intervertebral discs and ligaments, and can cause symptoms such as back pain, leg pain, and intermittent claudication. In order to treat the lumbar spinal canal stenosis, surgery for partially resecting the spine in a site causing the stenosed spinal canal (laminectomy) or a surgery for fixing the spine (spinal fusion surgery) can be performed. In contrast, as a surgical technique, which is relatively minimally invasive compared to the laminectomy or the spinal fusion surgery, a method, has been recently developed in which a metallic spacer is caused to indwell between spinous processes so as to release compression of spinal nerves or nerve roots. However, according to the method, it is necessary to resect back muscles and ligaments in order to cause the spacer to indwell. Consequently, a patient still feels that the surgery is very invasive, and can require longer medical treatment.

In order to solve this problem, an alternative method has been proposed in which a spacer is inserted into and caused to indwell between the spinous processes in a less invasive manner. For example, as the alternative method, U.S. Patent Application Publication No. 2009/0118833 discloses a method of using a dilatable balloon as the spacer. In this case, the balloon in a folded state is percutaneously inserted into the spinous processes. The inside of the balloon is filled with a filling material such as bone cement, and the balloon is dilated and caused to indwell the spinous processes. The filling material is cured after filling the balloon, and thus the balloon can semi-permanently maintain a dilated state.

SUMMARY

When a spacer is caused to indwell between spinous processes, the center of the spacer in an axial direction needs to be positioned at the center of interspinous ligaments between the adjacent spinous processes in a width direction. However, when a filling material is injected into a balloon configuring the spacer, in some cases, the spacer can be displaced from (slips out of) the spinous processes, and the center of the spacer in the axial direction can be unintentionally misaligned with the center of the interspinous ligaments in a width direction.

For example, if a filling material having a relatively high viscosity is introduced into the balloon, the balloon can be pressed against surrounding tissues (bones, muscles, and ligaments), thereby causing any one of a distal side and a proximal side of the balloon to be filled with the filling material earlier. Then, the balloon starts to dilate from the side on which the balloon is filled with the filling material earlier. Consequently, the spacer is displaced to the side, which starts to dilate earlier.

For example, when the distal side of the balloon dilates earlier, the proximal side of the balloon does not come in contact with the spinous processes (interspinous ligaments), but the distal side of the balloon comes into contact with the spinous processes. Then, a reaction force acting in a direction toward the distal side is applied to the balloon from the spinous processes. Consequently, the spacer is relatively displaced to the distal side from the spinous processes.

Similarly, for example, when the proximal side of the balloon dilates earlier, the distal side of the balloon does not come in contact with the spinous processes, but the proximal side of the balloon comes into contact with the spinous processes. Then, the reaction force acting in a direction toward the proximal side can be applied to the balloon from the spinous processes. Consequently, the spacer is relatively displaced to the proximal side from the spinous processes.

In accordance with an exemplary embodiment, this displacement can occur when the spacer has an uneven shape, such as a so-called H-shape or dumbbell shape. Then, if the spacer is displaced from the spinous processes, the spacer may be detached from a space between the spinous processes.

A spacer is disclosed, which can help prevent the spacer from being displaced when the spacer is caused to indwell between bones, and to provide an implant assembly including the same, a manufacturing method of a spacer, and a surgical method for spacer indwelling.

According to the present disclosure, a spacer is disclosed which indwells between bones so as to expand a space between the bones. The spacer can include an outer balloon that is folded so as to be dilatable, and an inner balloon that is folded so as to be dilatable, and that is removably inserted into the outer balloon. The inner balloon dilates in response to the introduction of a dilating fluid, which has a lower viscosity than a viscosity of a filling material introduced into the outer balloon. The outer balloon dilates in response to the dilation of the inner balloon.

According to the spacer in the present disclosure, if the dilating fluid having the viscosity which is lower than the viscosity of the filling material is introduced into the inner balloon, the entire body of the inner balloon is filled with the dilating fluid at substantially the same time. Then, the entire body of the inner balloon dilates at substantially the same time. Accordingly, in response to the dilation of the inner balloon, the entire body of the outer balloon firstly dilates at substantially the same time, which helps prevent any one of the distal side and the proximal side of the outer balloon from firstly dilating earlier. Accordingly, the outer balloon can be prevented from being displaced when the outer balloon firstly dilates. At this stage, the outer balloon dilates (is deployed) while at least a portion of the folded portion of the outer balloon presses the surrounding tissues.

In addition, the inner balloon deflates by absorbing (pulling out) the dilating fluid, which helps enable the inner balloon to be removed from the firstly dilated outer balloon. At this time, there is no possibility that the firstly dilated outer balloon may be folded again. Therefore, if the filling material is introduced into the firstly dilated outer balloon, the entire body of the outer balloon secondly dilates at substantially the same time, which can help prevent any one of the distal side and the proximal side of the outer balloon from secondly dilating earlier. Accordingly, it is possible to prevent the spacer from being displaced when the spacer is caused to indwell between bones.

In the above-described spacer, in a deflated state of the inner balloon, multiple first folded portions which are bent in the same circumferential direction may be formed at multiple locations in the circumferential direction. In a deflated state of the outer balloon, multiple second folded portions which are bent in the same circumferential direction may be formed at multiple locations in the circumferential direction. A bending direction of the respective first folded portions and a bending direction of the respective second folded portions may be the same as each other.

According to this configuration, if the inner balloon dilates, the respective first folded portions dilate while rotating in the direction opposite to the bending direction. In addition, if the outer balloon firstly dilates, the respective second folded portions dilate while rotating in the direction opposite to the bending direction. Then, the bending direction of the respective first folded portions and the bending direction of the respective second folded portions are the same as each other. Then, the rotating direction of the respective first folded portions when the inner balloon dilates and the rotating direction of the respective second folded portions when the outer balloon firstly dilates are the same as each other. In this manner, for example, compared to a case where the bending direction of the respective first folded portions and the bending direction of the respective second folded portions are opposite to each other, the outer balloon can smoothly and firstly dilate.

In the above-described spacer, in a deflated state of the inner balloon, multiple first folded portions which are bent in the same circumferential direction may be formed at multiple locations in the circumferential direction. In a deflated state of the outer balloon, multiple second folded portions, which are bent in the same circumferential direction may be formed at multiple locations in the circumferential direction. A bending direction of the respective first folded portions and a bending direction of the respective second folded portions may be opposite to each other.

According to this configuration, the bending direction of the respective first folded portions configuring the inner balloon and the bending direction of the respective second folded portions configuring the outer balloon are opposite to each other. Therefore, the rotating direction of the respective first folded portions when the inner balloon dilates and the rotating direction of the respective second folded portions when the outer balloon firstly dilates are opposite to each other. In this manner, compared to a case where the bending direction of the respective first folded portions and the bending direction of the respective second folded portions are the same as each other, the outer balloon can be prevented from rotating around the axis when the outer balloon firstly dilates. Accordingly, the outer balloon can effectively be prevented from being displaced when the outer balloon firstly dilates.

In the above-described spacer, in a deflated state of the outer balloon, a lumen in which the deflated inner balloon is to be arranged may be formed in a central portion of the outer balloon. The respective first folded portions may be arranged in the lumen without being interposed between the respective second folded portions.

According to this configuration, in a state where the spacer deflates, the respective first folded portions of the inner balloon are arranged in the lumen in the central portion of the outer balloon without being interposed between the respective second folded portions of the outer balloon. Therefore, when the inner balloon is dilated, the respective first folded portions can be relatively rotated with respect to the outer balloon. In this manner, for example, compared to a case where the respective first folded portions are interposed between the respective second folded portions, a configuration can be adopted in which a rotational force of the respective first folded portions when the inner balloon dilates is less likely to be transmitted to the outer balloon. Accordingly, the outer balloon can be prevented from being displaced by the outer balloon being rotated when the outer balloon firstly dilates.

In the above-described spacer, a position of the multiple first folded portions in the circumferential direction and a position of the multiple second folded portions in the circumferential direction may correspond to each other.

According to this configuration, the respective first folded portions which are dilated by the dilating fluid to dilate by contacting with the respective second folded portions of the outer balloon can occur. In this manner, the outer balloon can be more smoothly and firstly dilate.

In the above-described spacer, the inner balloon in a dilated state may have a cylindrical shape. The outer balloon in a dilated state may have a shape having a neck portion and bulged portions disposed on both sides of the neck portion.

According to this configuration, a configuration can be adopted in which the outer balloon in the first dilated state has the same cylindrical shape as the inner balloon in the dilated state. In this manner, for example, compared to a case where the shape when the inner balloon dilates is set to be the shape when the outer balloon dilates (shape including the neck portion and the pair of bulged portions), an amount of rotation around the axis of the outer balloon can be reduced. Accordingly, the outer balloon can be efficiently prevented from being displaced when the outer balloon firstly dilates. In addition, the pair of bulged portions is formed in a secondly dilated state of the outer balloon. Therefore, the outer balloon which secondly dilates can be prevented from slipping out from a space between bones.

In the above-described spacer, a holding fluid for maintaining a dilated state of the outer balloon when the inner balloon is deflated by pulling the dilating fluid out of the inner balloon may be introduced into a portion between the inner balloon and the outer balloon. There may be further provided an outflow portion which causes the holding fluid inside the outer balloon to flow outward, in response to the filling material being introduced into the outer balloon whose dilated state is maintained.

According to an exemplary embodiment, the firstly dilated state of the outer balloon can be maintained when the inner balloon is deflated by pulling out the dilating fluid. In this manner, for example, the deflated inner balloon can be easily removed from the outer balloon. In addition, during the removal, the outer balloon maintains the firstly dilated state. Therefore, a reaction force acting from the surrounding tissues can hold the outer balloon. Accordingly, the outer balloon can be reliably prevented from being displaced when the outer balloon secondly dilates. Furthermore, since the outflow portion is provided, the filling material can be easily introduced into the outer balloon which maintains the firstly dilated state.

In accordance with an exemplary embodiment, in the above-described spacer, the filling material may be introduced from a proximal end of the outer balloon. The outflow portion may be disposed in a distal end of the outer balloon. In this case, the filling material introduced from the proximal end of the outer balloon presses the holding fluid forward to the outflow portion which is disposed in the distal end of the outer balloon. In this manner, for example, the holding fluid can be smoothly pulled out of the outer balloon.

In the above-described spacer, the outflow portion may allow circulation of the holding fluid having a predetermined pressure or greater, and may block the circulation of the filling material and the holding fluid having a pressure which is smaller than the predetermined pressure.

According to an exemplary embodiment, before the filling material is introduced into the outer balloon, the holding fluid can be prevented from flowing outward from the outer balloon via the outflow portion. In this manner, for example, the holding fluid can preferably maintain the firstly dilated state of the outer balloon. In addition, when the pressure of the holding fluid increases, since the filling material is introduced into the outer balloon, the holding fluid can reliably flow out from the outer balloon via the outflow portion. In this case, the filling material can be prevented from leaking out from the outer balloon.

An implant assembly is disclosed, which can include a spacer that indwells between bones so as to function as an implant for expanding a space between the bones, a catheter tube that is detachably connected to a proximal end of the spacer, and a hub that is connected to a proximal end of the catheter tube. In accordance with an exemplary embodiment, the spacer is a spacer disclosed herein.

A manufacturing method is disclosed of a spacer, which can include a first forming step of forming a first pleated portion which radially protrudes at multiple locations in a circumferential direction of an inner balloon by folding inner surfaces at the respective locations so as to come into contact with each other, a first bending step of forming multiple first folded portions by bending the respective first pleated portions in the same circumferential direction, an inserting step of inserting the inner balloon which is folded in the first forming step and the first bending step into an outer balloon which is not folded, a second forming step of forming a second pleated portion which radially protrudes at multiple locations in a circumferential direction of an outer balloon by folding inner surfaces at the respective locations so as to come into contact with each other, and a second bending step of forming multiple second folded portions by bending the respective second pleated portions in the same circumferential direction.

According to the manufacturing method of the spacer in the present disclosure, the spacer can be easily manufactured in which the inner balloon having the multiple first folded portions is accommodated inside the outer balloon having the multiple second folded portions.

In the above-described manufacturing method, in the second bending step, the respective second pleated portions may be bent in the same direction as a bending direction of the respective first pleated portions. In this case, for example, the bending direction of the respective first folded portions configuring the inner balloon and the bending direction of the respective second folded portions configuring the outer balloon can be easily set to be the same direction as each other.

In the above-described manufacturing method, in the second bending step, the respective second pleated portions may be bent in a direction opposite to a bending direction of the respective first pleated portions. In this case, for example, the bending direction of the respective first folded portions configuring the inner balloon and the bending direction of the respective second folded portions configuring the outer balloon can be easily set to be directions opposite to each other.

A surgical method is disclosed for spacer indwelling in which a spacer indwells between bones so as to expand a space between the bones. The surgical method for spacer indwelling can include a spacer inserting step of inserting the spacer including an outer balloon that is folded so as to be dilatable and an inner balloon that is folded so as to be dilatable and that is inserted into the outer balloon, into the space between the bones, a first dilating step of dilating the inner balloon by introducing a dilating fluid having lower viscosity than the viscosity of a filling material into the inner balloon, and of firstly dilating the outer balloon in response to the dilation of the inner balloon, a dilating fluid pulling-out step of deflating the inner balloon by pulling the dilating fluid out of the inside of the inner balloon, a removing step of removing the deflated inner balloon from the outer balloon, and a second dilating step of secondly dilating the outer balloon by introducing the filling material into the outer balloon.

According to the surgical method for spacer indwelling in the present disclosure, the dilating fluid having the viscosity which is lower than the viscosity of the filling material is introduced into the inner balloon. Therefore, the entire body of the outer balloon can firstly dilate at substantially the same time in response to the dilation of the inner balloon. In accordance with an exemplary embodiment, for example, any one of the distal side and the proximal side of the outer balloon can be prevented from firstly dilating earlier. Accordingly, the outer balloon can be prevented from being displaced when the outer balloon firstly dilates. At this stage, the outer balloon dilates (is deployed) while at least a portion of the folded portion of the outer balloon presses the surrounding tissues.

In addition, when the inner balloon deflated by pulling out the dilating fluid is removed from the firstly dilated outer balloon, there is no possibility that the outer balloon may be folded again. Therefore, the entire body of the outer balloon can secondly dilate at substantially the same time by introducing the filling material into the firstly dilated outer balloon. In this manner, any one of the distal side and the proximal side of the outer balloon can be prevented from secondly dilating earlier. Accordingly, the spacer can be prevented from being displaced when the spacer is caused to indwell between bones.

The surgical method for spacer indwelling may further include a holding fluid introducing step of maintaining a dilated state of the outer balloon by introducing a holding fluid into a portion between the inner balloon which is deflated in the dilating fluid pulling-out step and the outer balloon. In the second dilating step, the holding fluid inside the outer balloon may be caused to flow outward via an outflow portion, in response to the filling material being introduced into the outer balloon.

According to this method, since the holding fluid introducing step is performed, the outer balloon maintains the dilated state (firstly dilated state) when the inner balloon is removed from the outer balloon. In this manner, it becomes relatively easy to remove the deflated inner balloon from the outer balloon. In addition, during the removal, a reaction force acting from the surrounding tissues holds the outer balloon. Therefore, the outer balloon can reliably be prevented from being displaced when the outer balloon secondly dilates. Furthermore, in the second dilating step, the holding fluid is caused to flow outward via the outflow portion. Accordingly, the filling material can easily be introduced into the outer balloon which maintains the firstly dilated state.

BRIEF DESCRIPTION OF THE DRAWINGS

FIG. 17A is a longitudinal sectional view illustrating a first configuration example in an outer balloon.

FIG. 17B is a longitudinal sectional view illustrating a second configuration example in the outer balloon.

FIG. 17C is a longitudinal sectional view illustrating a third configuration example in the outer balloon.

FIG. 17D is a longitudinal sectional view illustrating a fourth configuration example in the outer balloon.

FIG. 17E is a longitudinal sectional view illustrating a fifth configuration example in the outer balloon.

FIG. 17F is a longitudinal sectional view illustrating a sixth configuration example in the outer balloon.

DETAILED DESCRIPTION

Hereinafter, a spacer and an implant assembly including the same according to the present disclosure will be described with reference to the accompanying drawings. Preferred embodiments will be described as an example in association with a manufacturing method of the spacer and a surgical method for spacer indwelling.

Figure 1:
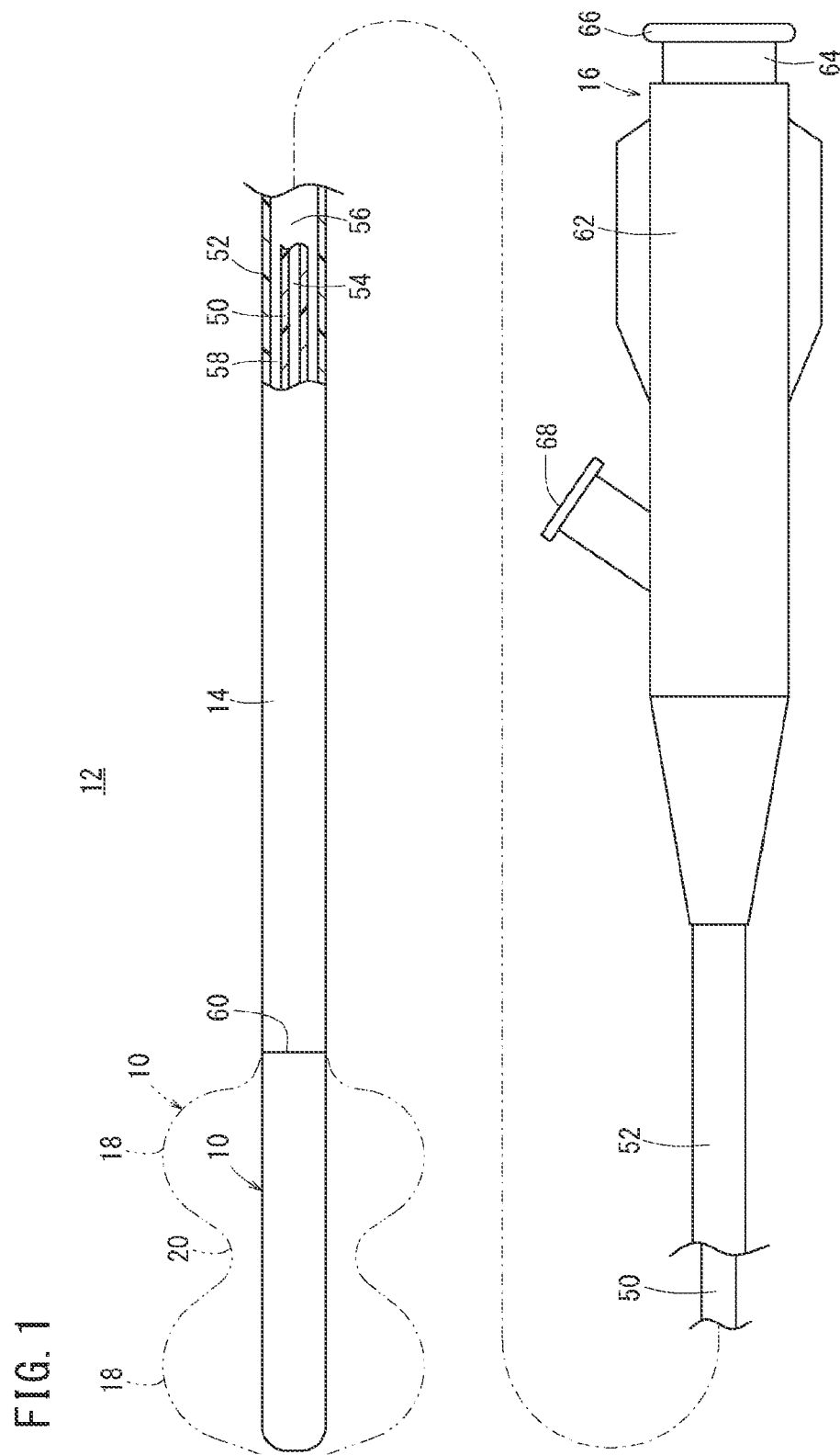
FIG. 1 is a sectional side view of a partially omitted implant assembly according to an embodiment of the present invention.

As illustrated in FIG. 1, an implant assembly 12 according to the present exemplary embodiment can include a spacer 10 which is disposed in an distal end of the implant assembly 12, a catheter tube (hereinafter, referred to as a "tube") 14 which is connected to a proximal side of the spacer 10, and a hub 16 which is connected to a proximal end of the tube 14.

The spacer 10 functions as an implant (spacer implant) which is inserted into a living body so as to indwell the living body, and is configured to be dilatable by a fluid which is introduced into the spacer 10. For example, living body sites to which the spacer 10 is inserted include spinous processes, shoulder joints, and intervertebral discs. In an initial state, the spacer 10 deflates as illustrated by a solid line in FIG. 1. In contrast, if the spacer 10 is filled with a filling material 74 via the tube 14, the spacer 10 dilates as illustrated by a virtual line in FIG. 1.

Figure 10A:
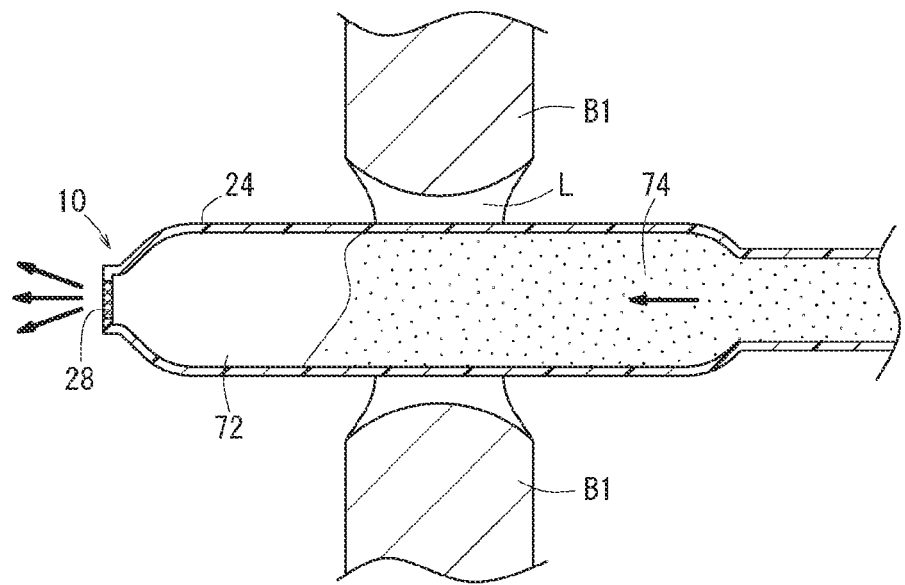
FIG. 10A is a view for describing a filling material introducing step and a holding fluid pulling-out step according to the surgical method for spacer indwelling.
Figure 10B:
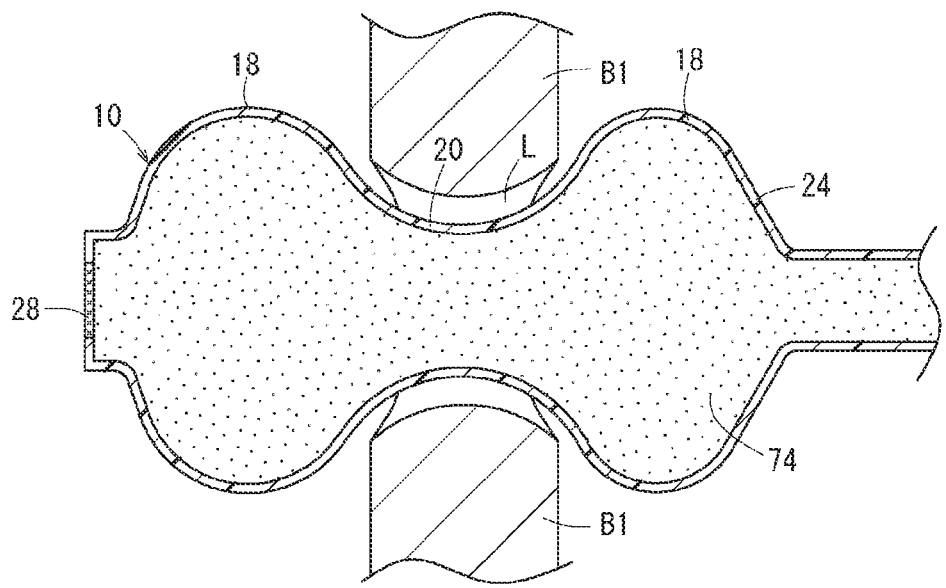
FIG. 10B is a second dilating step according to the surgical method for spacer indwelling.

For example, as illustrated in FIG. 1, a dilated shape of the spacer 10 can employ a shape in which a pair of bulged portions 18 are connected to each other via a neck portion 20. If the dilated shape of the spacer 10 employs shapes such as a dumbbell shape, a wheel shape (H-shape), and the like, this shape preferably allows an interspinous ligament to be interposed therebetween (refer to FIG. 10B).

Figure 2A:
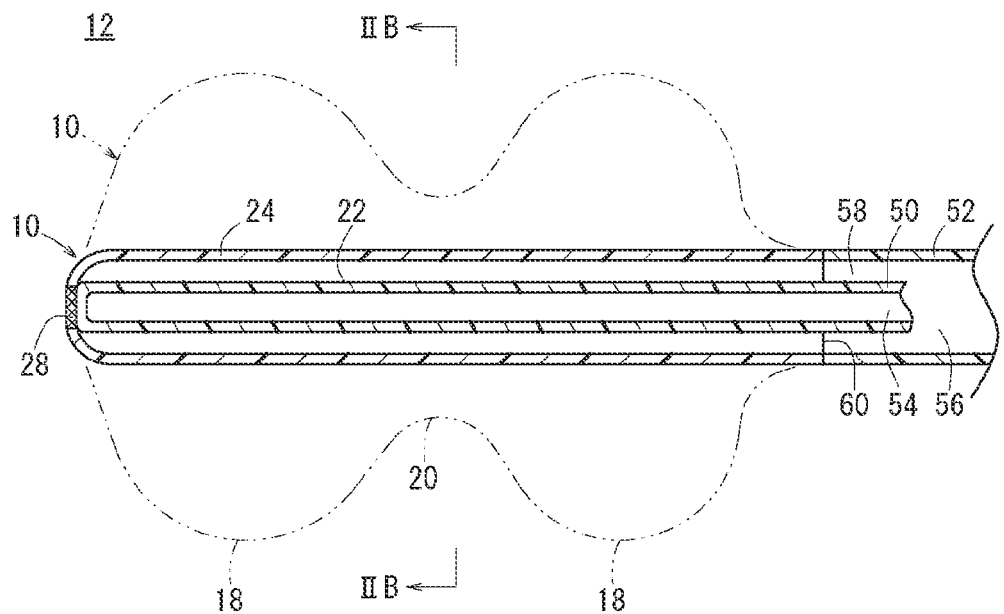
FIG. 2A is a schematic longitudinal sectional view of a spacer configuring the implant assembly illustrated in FIG. 1.

As illustrated in FIG. 2A, the spacer 10 can include an inner balloon 22 which dilates in response to the introduction of a dilating fluid 70 (refer to FIG. 9A), an outer balloon 24 which accommodates the inner balloon 22 and firstly dilates in response to the dilation of the inner balloon 22, and an outflow portion 28.

Herein, a procedure of dilating the spacer 10 according to the present embodiment will be briefly described. First, the spacer 10 in a deflated state is inserted into spinous processes, and the dilating fluid 70 is introduced into the inner balloon 22. Then, the inner balloon 22 dilates, and the outer balloon 24 firstly dilates (refer to FIG. 9A).

Figure 9A:
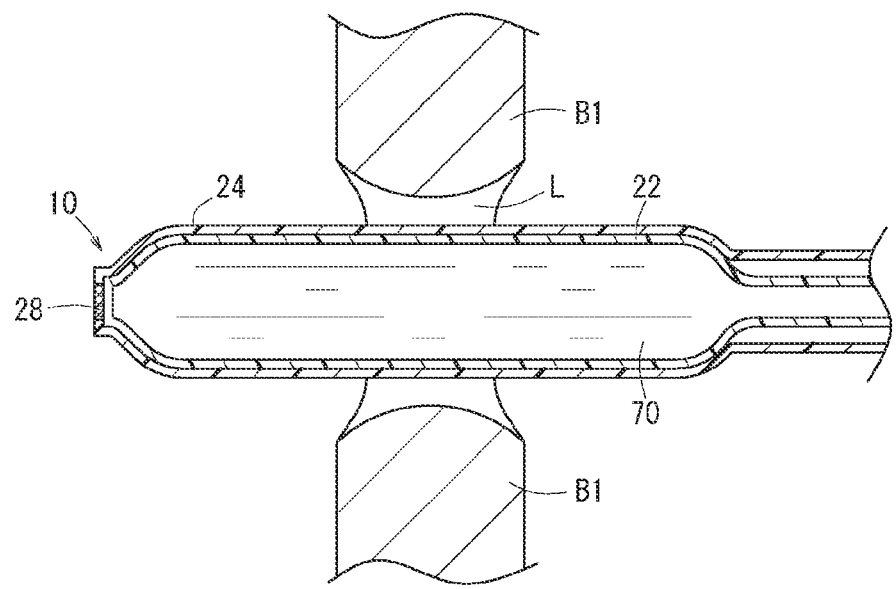
FIG. 9A is a view for describing a first dilating step according to the surgical method for spacer indwelling.
Figure 9B:
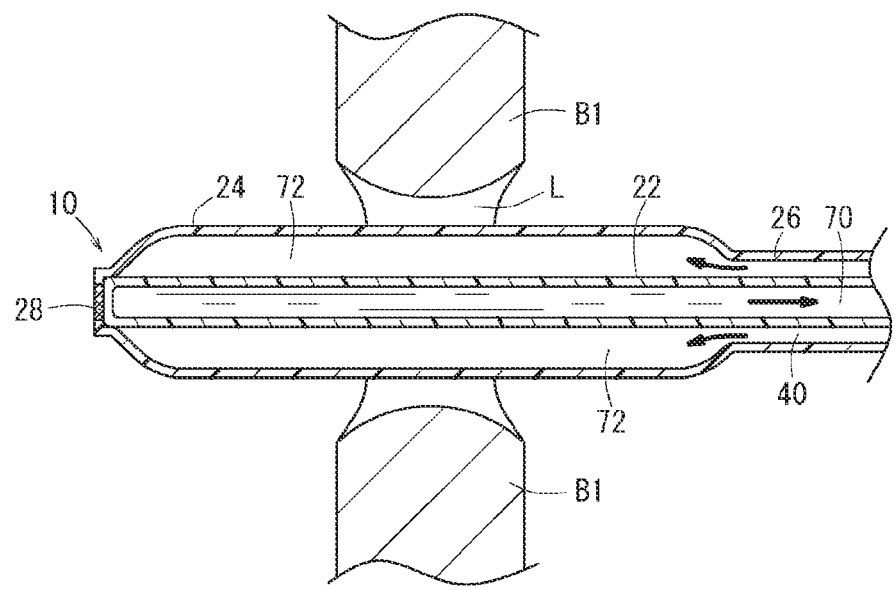
FIG. 9B is a holding fluid introducing step and a dilating fluid pulling-out step according to the surgical method for spacer indwelling.

Then, the dilating fluid 70 is pulled out of the inner balloon 22, and a holding fluid 72 is introduced into a portion between the firstly dilated outer balloon 24 and the inner balloon 22 (refer to FIG. 9B). In this manner, the inner balloon 22 deflates while the outer balloon 24 maintains a firstly dilated state.

Subsequently, the inner balloon 22 is removed from the outer balloon 24. Thereafter, the filling material 74 is introduced into the outer balloon 24, and the holding fluid 72 is caused to flow outward from the outer balloon 24 via the outflow portion 28 (refer to FIG. 10A). Then, the outer balloon 24 filled with the filling material 74 secondly dilates (refer to FIG. 10B). In this manner, a space between the spinous processes expands, and the spacer 10 can be indwelled between the spinous processes.

Next, a configuration of the spacer 10 according to the present exemplary embodiment will be described. The inner balloon 22 to be inserted into the outer balloon 24 is configured to have a bag shape. In a deflated state, the inner balloon 22 is folded so as to be dilatable, shows an elongated tube shape, and extends over the entire length of the outer balloon 24.

Figure 2B:
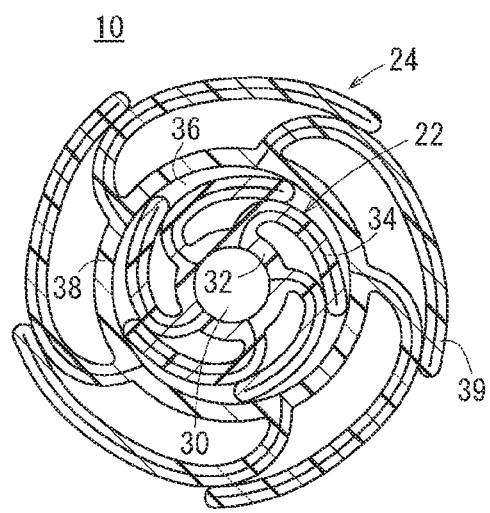
FIG. 2B is a horizontal sectional view taken along line IIB-IIB in FIG. 2A.
Figure 3:
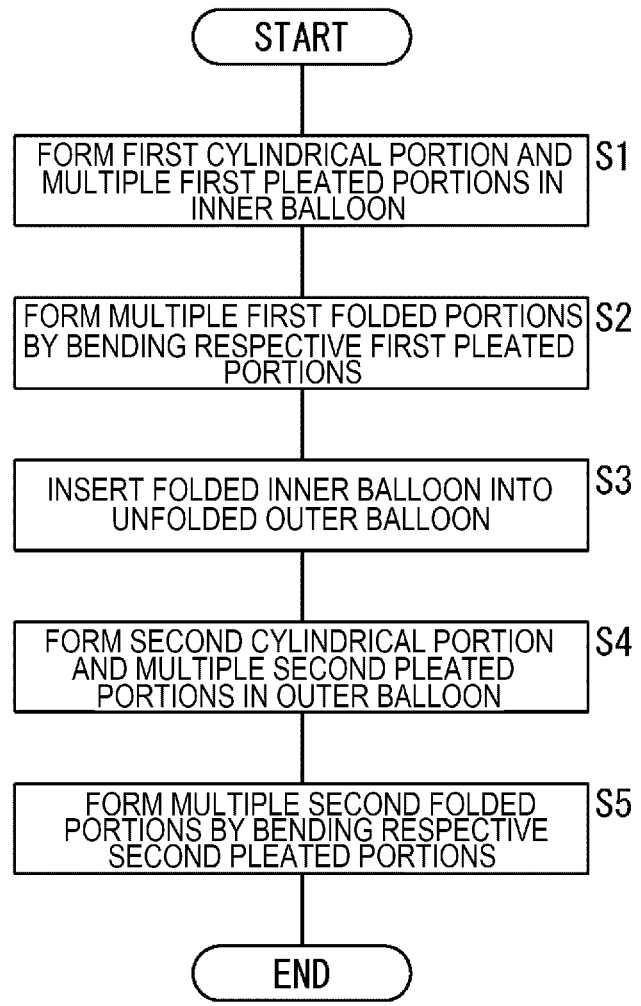
FIG. 3 is a flowchart illustrating a procedure of a manufacturing method of a spacer.

As illustrated in FIG. 2B, the inner balloon 22 in the deflated state has a first cylindrical portion 32 having a lumen 30 for circulating the dilating fluid 70, and multiple (five in the present embodiment) first folded portions 34 which are disposed at multiple locations in the circumferential direction of the first cylindrical portion 32 and which are bent in the same circumferential direction (clockwise in the illustrated example).

The multiple first folded portions 34 can extend over substantially the entire length of the inner balloon 22, and can be disposed at equal intervals in the circumferential direction. The respective first folded portions 34 overlap the adjacent first folded portions 34, and an outer shape extending along a horizontal section of the inner balloon 22 can be a substantially circular shape. As a matter of course, a shape, a size, or the like of the respective first folded portions 34 can be optionally set.

If the dilating fluid 70 is introduced into the first cylindrical portion 32 of the inner balloon 22, the respective first folded portions 34 dilate (are deployed), and dilate so as to have a preset shape and size. In the present exemplary embodiment, the shape of the dilated inner balloon 22 is a cylindrical shape (refer to FIG. 9A). However, the shape of the dilated inner balloon 22 can be optionally set. For example, the dilated inner balloon 22 may be formed into a dumbbell shape or a wheel shape (H-shape).

In accordance with an exemplary embodiment, the inner balloon 22 can be configured to include materials which can dilate the outer balloon 24 and can withstand external pressure generated by the surrounding tissues such as tissues of spinous processes, interspinous ligaments, and the like when the dilating fluid 70 is injected into the inner balloon 22. For example, these materials can include vinyl chloride, polyurethanes, polyurethane elastomers, nylon, polyethylene terephthalate (PET), polyester or a polyester elastomer containing polyester such as poly butylene terephthalate (PBT) or the like, polyamide resin or polyamide elastomer containing polyamide resin such as nylon 11, nylon 12, nylon 610, polymeric materials such as polytetrafluoroethylene (PTFE, ePTFE), and a mixture of these materials.

In accordance with an exemplary embodiment, the outer balloon 24 can be configured to have a bag shape. The outer balloon 24 in a deflated state is folded so as to be dilatable, and shows an elongated tube shape. The outer balloon 24 in the deflated state has a second cylindrical portion 38 having a lumen 36 in which the deflated inner balloon 22 is to be arranged, and multiple (for example, five in the present embodiment) second folded portions 39 which are disposed at multiple locations in the circumferential direction of the second cylindrical portion 38 and which are bent in the same circumferential direction (clockwise in the illustrated example).

The multiple second folded portions 39 extend over substantially the entire length of the outer balloon 24, and are disposed at equal intervals in the circumferential direction. The respective second folded portions 39 overlap the adjacent second folded portions 39, and an outer shape extending along a horizontal section of the outer balloon 24 is a substantially circular shape. As a matter of course, a shape, a size, or the like of the respective second folded portions 39 can be optionally set.

In accordance with an exemplary embodiment, if the inner balloon 22 accommodated in the outer balloon 24 dilates, the respective second folded portions 39 partially dilate (are deployed) so as to be widely pressed against the inner balloon 22, and firstly dilate so as to have the same shape as the inner balloon 22 and a larger size than the inner balloon 22 (refer to FIG. 9A). In the present exemplary embodiment, the firstly dilated outer balloon 24 has a cylindrical shape. In addition, if the firstly dilated outer balloon 24 is filled with the filling material 74, the respective second folded portions 39 completely dilate (are deployed), and secondly dilate so as to have a preset shape and size. In the present embodiment, the shape of the secondly dilated outer balloon 24 is a dumbbell shape having the neck portion 20 between the pair of bulged portions 18 (refer to FIG. 10B). However, in accordance with an exemplary embodiment, for example, the shape of the secondly dilated outer balloon 24 can be optionally set.

The outer balloon 24 can be configured to include the same materials as the inner balloon 22, but is configured to include materials which withstand not only external pressure generated by the surrounding tissues such as tissues of spinous processes, interspinous ligaments, and the like, but also external pressure generated in response to the movement of the vertebral body. In this case, for example, the inner balloon 22 and the outer balloon 24 may be configured to include the same material, or may be configured to include mutually different materials.

In the inner balloon 22 and the outer balloon 24 which are described above, the inner balloon 22 in a deflated state is wound by the folded outer balloon 24. Therefore, the movement of the inner balloon 22 along the axial direction is regulated with respect to the outer balloon 24. In contrast, in a state where the inner balloon 22 dilates in response to the introduction of the dilating fluid and the outer balloon 24 firstly dilates, the outer balloon 24 releases the regulation of the movement of the inner balloon 22. Accordingly, the inner balloon 22 can be removed from the outer balloon 24. In accordance with an exemplary embodiment, for example, in the present exemplary embodiment, the inner balloon 22 is inserted into the outer balloon 24 so as to be removable from the outer balloon 24.

In accordance with an exemplary embodiment, the outflow portion 28 causes the holding fluid 72 inside the outer balloon 24 to flow outward in response to the filling material 74 being introduced into the firstly dilated outer balloon 24, and is disposed in the distal portion of the outer balloon 24 (refer to FIG. 2A). The outflow portion 28 is configured to include a ventilation member which allows circulation of the holding fluid 72 having a predetermined pressure or greater, and which blocks the circulation of the filling material 74 and the holding fluid 72 having a lower pressure than the predetermined pressure. In this manner, the holding fluid 72 can maintain the firstly dilated state of the outer balloon 24, and the filling material 74 injected into the outer balloon 24 can be prevented from leaking from the outer balloon 24.

Subsequently, a manufacturing method of the above-described spacer 10 will be described with reference to FIGS. 2B, and 3 to 5B.

First, multiple locations (five locations in FIG. 4B) in the circumferential direction of the inner balloon 22 which has an unfolded bag shape (refer to FIG. 4A) are folded so that inner surfaces of the respective locations come into contact with each other. In accordance with an exemplary embodiment, for example, the first cylindrical portion 32 is formed around the center of the inner balloon 22, and a first pleated portion 42 radially protruding is formed at multiple locations in the circumferential direction (Step S1: first forming step, refer to FIG. 4B). At this time, the multiple pleated portions 42 are located at equal intervals in the circumferential direction of the first cylindrical portion 32.

Figure 4A:
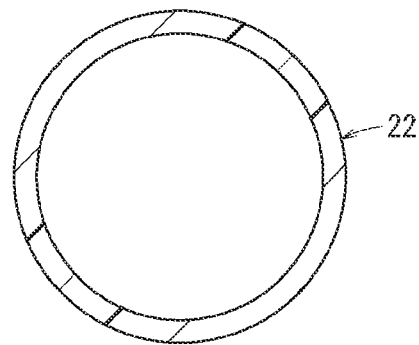
FIG. 4A is a first view for describing the manufacturing method of the spacer.
Figure 4B:
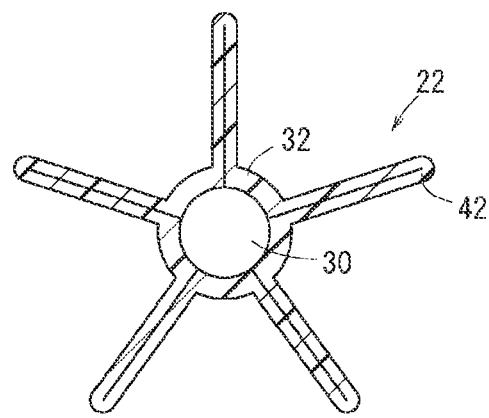
FIG. 4B is a second view for describing the manufacturing method of the spacer.
Figure 4C:
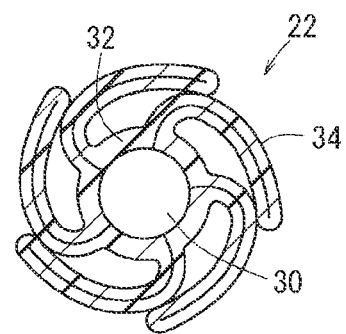
FIG. 4C is a third view for describing the manufacturing method of the spacer.

Subsequently, the respective first pleated portions 42 are bent in the same circumferential direction, and are brought into a folded state in the circumferential direction as illustrated in FIG. 4C (Step S2: first bending step). In this manner, the inner balloon 22 including the first cylindrical portion 32 and the multiple first folded portions 34 can be obtained.

Figure 5A:
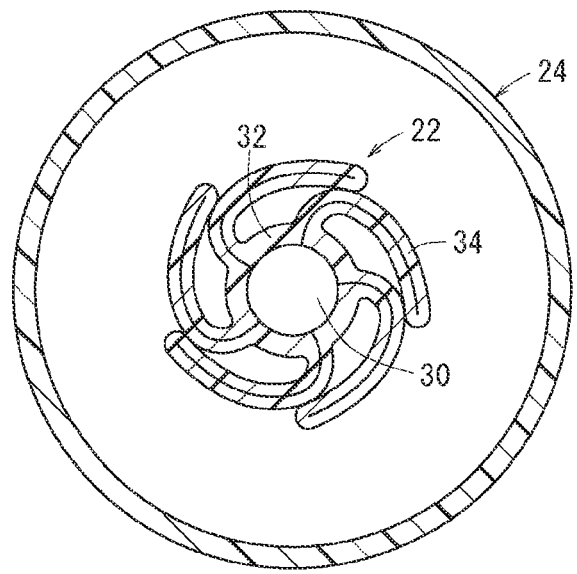
FIG. 5A is a fourth view for describing the manufacturing method of the spacer.
Figure 5B:
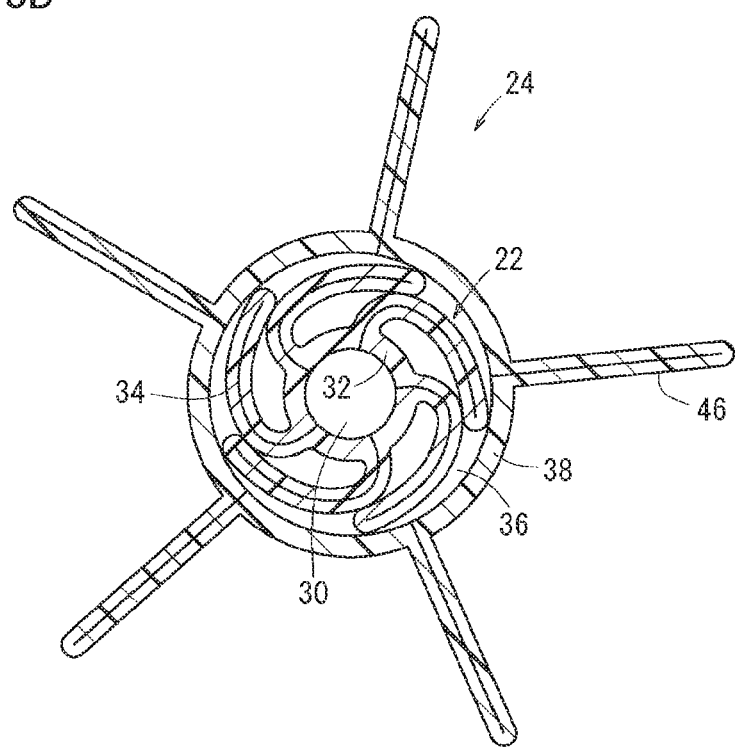
FIG. 5B is a fifth view for describing the manufacturing method of the spacer.
Figure 6:
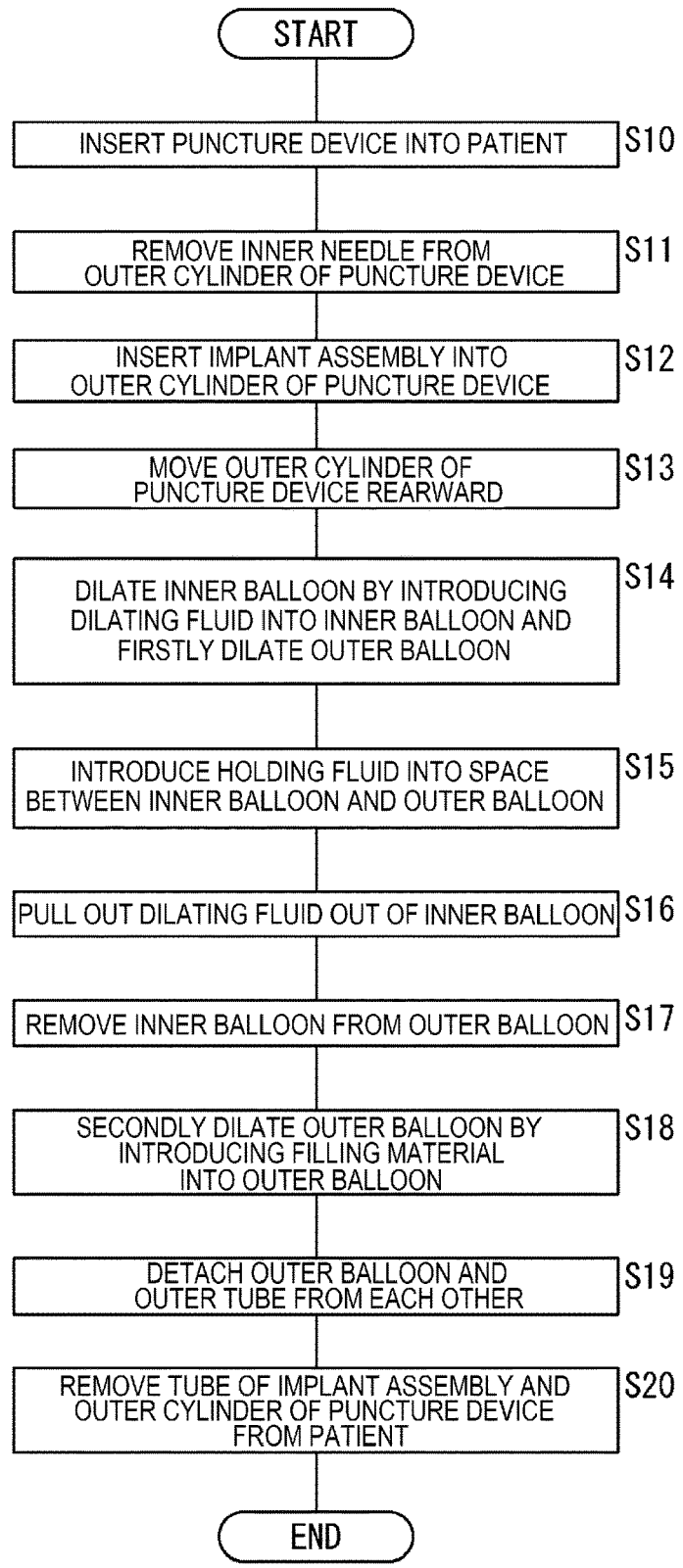
FIG. 6 is a flowchart illustrating a procedure of a method in which a spacer is inserted into and caused to indwell between spinous processes (surgical method for spacer indwelling).

Next, the folded inner balloon 22 is inserted into the outer balloon 24 having an unfolded bag shape as illustrated in FIG. 5A (Step S3: inserting step). At this time, the distal end of the inner balloon 22 is brought into contact with the distal end of the outer balloon 24.

Then, multiple locations (five locations in FIG. 5B) in the circumferential direction of the outer balloon 24 into which the inner balloon 22 is inserted are folded so that inner surfaces of the respective locations come into contact with each other. In accordance with an exemplary embodiment, for example, the second cylindrical portion 38 is formed around the center of the outer balloon 24, and a second pleated portion 46 radially protruding is formed at multiple locations in the circumferential direction (Step S4: second forming step, refer to FIG. 5B). At this time, the multiple second pleated portions 46 are located at equal intervals in the circumferential direction of the second cylindrical portion 38, and the outer balloon 24 is folded so that the circumferential position of the respective second pleated portions 46 corresponds to the circumferential position of the respective first folded portions 34.

Thereafter, the respective second pleated portions 46 are bent in the same circumferential direction, and are brought into a folded state in the circumferential direction as illustrated in FIG. 2B (Step S5: second bending step). At this time, the respective second pleated portions 46 are bent in the same direction as the bending direction of the respective first pleated portions 42. In this manner, it is possible to obtain the outer balloon 24 including the second cylindrical portion 38 and the multiple second folded portions 39. At this stage, the spacer 10 according to the present embodiment is completely manufactured.

As illustrated in FIG. 1, the tube 14 has a double tube structure in which an inner tube 50 is inserted into an outer tube 52. The tube 14 having the double tube structure including the inner tube 50 and the outer tube 52 is moderately flexible so that the tube 14 can be inserted into a bent puncture device 80 (to be described later, refer to FIG. 7A). For example, configuration materials of the inner tube 50 and the outer tube 52 can include polymeric materials such as polyolefin (for example, polyethylene, polypropylene, polybutene, ethylene-propylene copolymer, ethylene-vinyl acetate copolymer, ionomer, mixtures of these two or more materials), polyvinyl chloride, polyamides, polyesters, polyester elastomers, polyamide elastomers, polyurethanes, polyurethane elastomers, polyimides, polyether ether ketone (PEEK) nylon, polytetrafluoroethylene (PTFE, ePTFE), or a mixture of these materials.

The inner tube 50 can be an elongated tubular member having a thin diameter, and is connected to the proximal end of the inner balloon 22 (refer to FIG. 2A). The inner tube 50 has a lumen 54 which communicates with the inside (lumen) of the inner balloon 22 and which functions as a flow path of the dilating fluid 70. The lumen 54 opens from the distal end to the proximal end of the inner tube 50.

The outer tube 52 can be an elongated tubular member having a larger diameter than the inner tube 50, and is connected to the proximal end of the outer balloon 24. The outer tube 52 has a lumen 56 which communicates with the inside (lumen) of the outer balloon 24 and accommodates the inner tube 50. A lumen 58 which functions as a flow path of the holding fluid 72 is formed between an inner peripheral surface of the outer tube 52 and an outer peripheral surface of the inner tube 50. The lumen 58 communicates with a gap formed between the inner balloon 22 and the outer balloon 24.

The outer balloon 24 and the outer tube 52 are detachably connected to each other via a connection structure 60. For example, the connection structure 60 is a screw structure. When predetermined torques or greater are applied to the outer balloon 24 and the outer tube 52, both of these are unscrewed, thereby detaching the outer balloon 24 and the outer tube 52 from each other.

In addition to the above-described screw structure, the connection structure 60 can employ a structure in which both of these are detachably connected to each other by means of physical engagement (fitting or hooking), or a structure in which both of these are detachably connected to each other by dividing a member using some types of physical action (thermal action or chemical action).

The hub 16 has a hub body 62 which is connected to the proximal side of the outer tube 52, a slide hub 64 which is connected to the proximal end of the inner tube 50, a first port 66 which is disposed in the proximal end of the slide hub 64, and a second port 68 which is disposed in the hub body 62.

The hub body 62 and the slide hub 64 respectively have a hollow structure. The slide hub 64 in a state of movable rearward to the proximal side of the hub body 62 is inserted into the lumen on the proximal side of the hub body 62. If an operator (user) or the like grips the slide hub 64 and moves the slid hub 64 rearward to the proximal side of the hub body 62, the inner balloon 22 connected to the slide hub 64 via the inner tube 50 moves rearward to the proximal side of the outer balloon 24. In this manner, the inner balloon 22 can be removed from the outer balloon 24.

The first port 66 communicates with the lumen 54 of the inner tube 50, and is formed so as to be connectable to a dilating fluid supply source (not illustrated). The second port 68 communicates with the lumen 56 (lumen 58) of the outer tube 52, and is formed so as to be selectively connectable to a holding fluid supply source and a filling material supply source (both of these not illustrated). The dilating fluid supply source, the holding fluid supply source, and the filling material supply source are respectively configured to include a syringe, a pump, or an indeflator.

The dilating fluid 70 has lower viscosity than viscosity of the filling material 74. Types of the dilating fluid 70 can be optionally selected. However, for example, the present embodiment employs a contrast agent (non-hardening material). When the contrast agent is used as the dilating fluid 70, a position and a dilated state of the inflated inner balloon 22 (firstly dilated outer balloon 24) inside a living body can easily and reliably be recognized by using X-ray fluoroscopy.

In addition, in this case, the contrast agent is injected to the inner balloon 22. Accordingly, the contrast agent will not mix with the filling material 74, which is introduced into the outer balloon 24. In this manner, even when the curable filling material 74 is used, the contrast agent and the filling material 74 will not mix with each other and the curing reaction of the filling material 74 will not be inhibited. Accordingly, the rigidity of the filling material 74 can be substantially uniform.

The holding fluid 72 employs a fluid which does not affect a living body when the holding fluid 72 is pulled out of the outer balloon 24. This fluid can include, for example, air (compressed air).

The filling material 74 can employ either a material which is fluidic when injected and is cured after injected (for example, bone cement, acrylic resin, two-liquid mixing cross-linked polymer, or the like) or a material which is fluidic when injected and remains fluidic even after injected.

The implant assembly 12 including the spacer 10 according to the present exemplary embodiment can have the above-described configurations. Hereinafter, an operation and an advantageous effect will be described in association with a method of inserting the spacer 10 into spinous processes so that the spacer 10 indwells therebetween (surgical method for spacer indwelling).

Herein, a manual skill of using the puncture device 80 and percutaneously inserting the spacer 10 into the spinous processes, which are adjacent to each other in a living body so that the spacer 10 indwells therebetween will be described with reference to FIGS. 6 to 11B. Referring to FIGS. 7A to 11B, the reference numeral B represents a vertebra, and the reference numeral B1 represents a spinous process formed in the rear of the vertebra B.

Figure 7A:
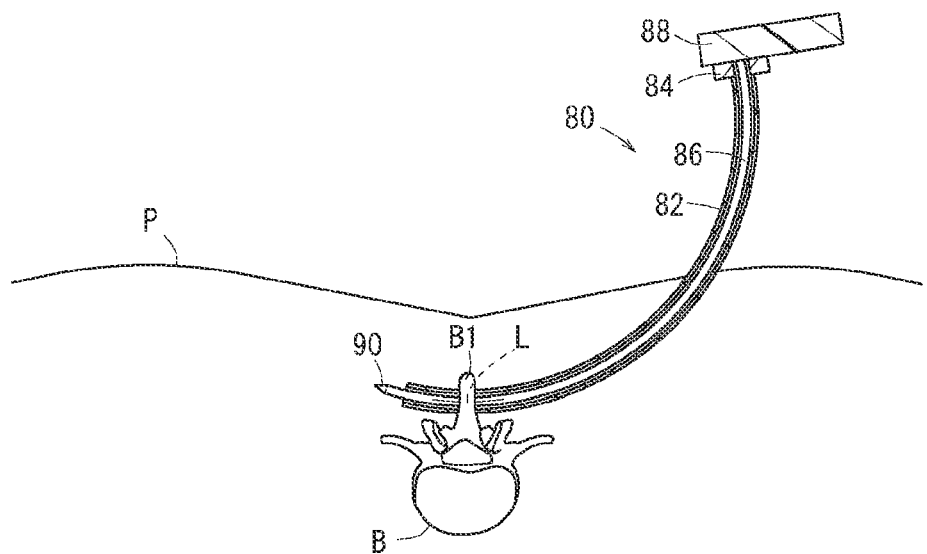
FIG. 7A is a view for describing an inserting step according to the surgical method for spacer indwelling.

Referring to FIG. 7A, the puncture device 80 has an outer cylinder 82, which has a hollow and arcuate shape, a hub 84 which is fixed to the proximal end of the outer cylinder 82, an inner needle 86 which can be inserted into the outer cylinder 82 and is formed in an arcuate shape having the same curvature as that of the outer cylinder 82, and a handle 88, which is fixed to the proximal end of the inner needle 86.

The outer cylinder 82 is a member whose both ends are open and which can include a hollow structure having a hollow portion into which the inner needle 86 can be inserted. The hub 84, which can be fixed to the proximal end of the outer cylinder 82 has an outer diameter larger than that of the outer cylinder 82, and is disposed in a flange shape.

The inner needle 86 can be a rod-like member which is inserted into the hollow portion of the outer cylinder 82, whose distal end has a sharp needlepoint 90, and which is curved in an arcuate shape. When the inner needle 86 is inserted into the outer cylinder 82 to the maximum degree, the distal end of the inner needle 86 protrudes from the distal end of the outer cylinder 82 by an amount of predetermined length. The inner needle 86 may have either a solid structure or a hollow structure. The handle 88, which is disposed in the proximal end of the inner needle 86 functions as a grip to be gripped by an operator.

An X-ray opaque marker may be installed in at least a portion of the outer cylinder 82 and the distal side of the inner needle 86 so as to be recognizable by using X-ray fluoroscope. In addition, without being limited to the puncture device 80 having the configuration illustrated in FIG. 7A, the puncture device 80 used together with the implant assembly 12 may employ a straight type of puncture device having a linear outer cylinder and inner needle, for example.

According to the surgical method for spacer indwelling, a lesion site is first determined by using an X-ray fluoroscopic apparatus, an MRI, an ultrasound diagnosis apparatus, or the like. Thereafter, a patient P is laid face down. Next, as illustrated in FIG. 7A, an operator inserts the puncture device 80 in a state where the inner needle 86 is inserted into the outer cylinder 82 into the patient P so as to reach a predetermined depth by using X-ray fluoroscope (Step S10 in FIG. 6: inserting step).

In the inserting step, for example, the outer cylinder 82 and the inner needle 86 of the puncture device 80 penetrate an interspinous ligament L between spinous processes B1 adjacent to each other, in a direction intersecting the axial direction of the spine. In this case, the puncture device 80 is inserted so as to reach a position where the distal portion of the puncture device 80 passes beyond the spinous processes B1 by an amount of predetermined length.

If the puncture device 80 is inserted by an amount of desired length, a position of the outer cylinder 82 is then held without any change, for example, the outer cylinder 82 remains inserted into the patient P. In this state, the inner needle 86 is removed from the outer cylinder 82 (Step S11: inner needle removing step). This causes the outer cylinder 82 in a state of being inserted into a living body to indwell the living body.

Figure 7B:
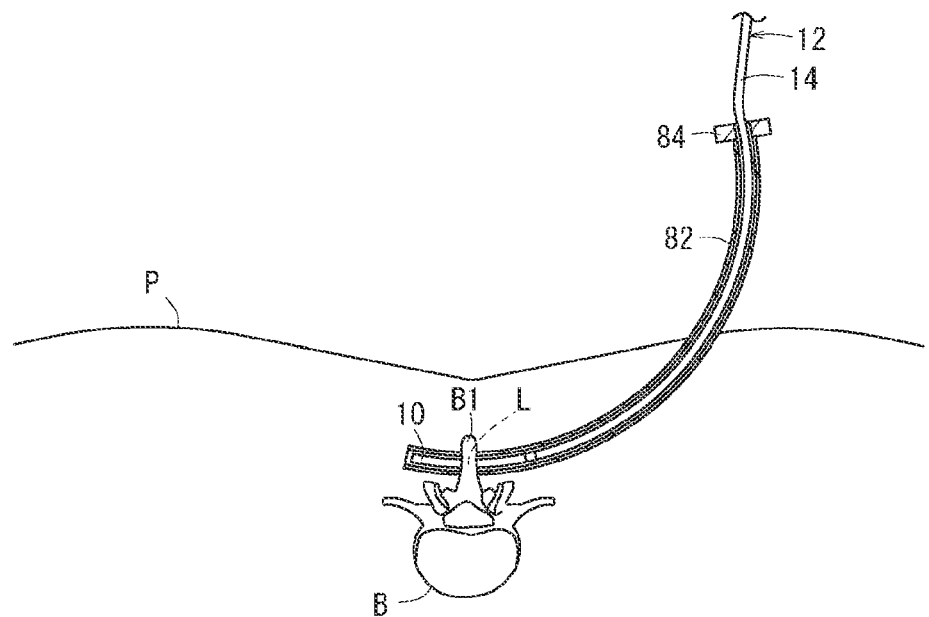
FIG. 7B is a view for describing a spacer inserting step according to the surgical method for spacer indwelling.

Subsequently, as illustrated in FIG. 7B, a distal end of the implant assembly 12, which is provided with the deflated spacer 10 is inserted into the hollow portion of the outer cylinder 82 (Step S12: spacer inserting step). In this spacer inserting step, for example, the implant assembly 12 is inserted so that the spacer 10 is located inside the distal portion of the outer cylinder 82 and the axial center of the spacer 10 is located at the center of the interspinous ligament L between the spinous processes B1 adjacent to each other. In this manner, the implant assembly 12 is inserted so as to reach a predetermined position inside the outer cylinder 82.

Figure 8A:
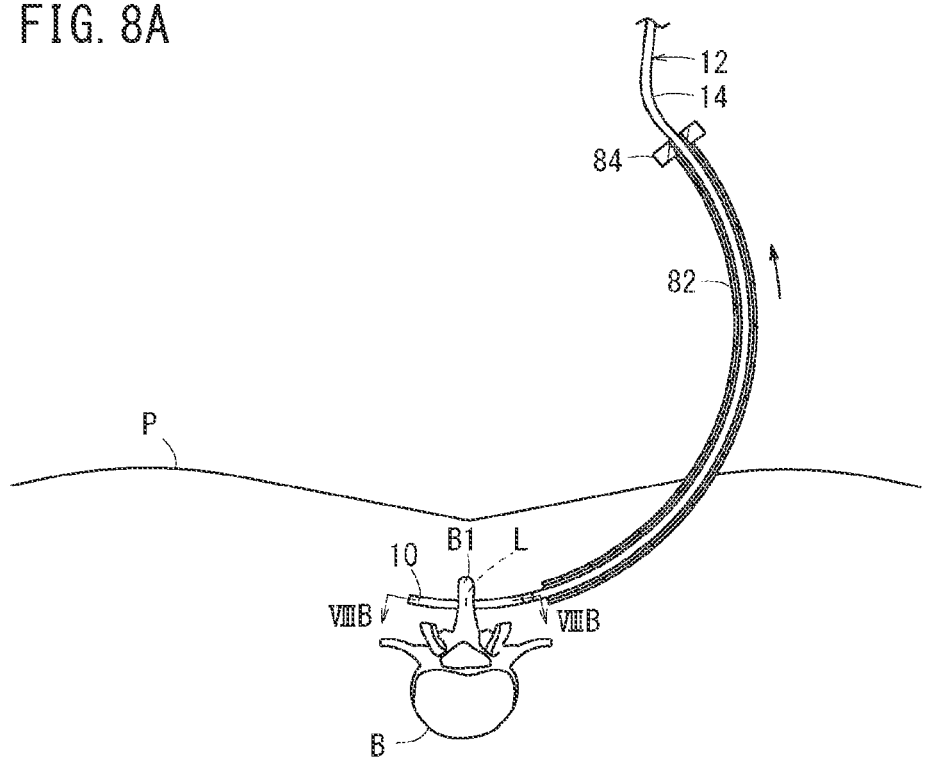
FIG. 8A is a view for describing a step of moving an outer cylinder rearward according to the surgical method for spacer indwelling.
Figure 8B:
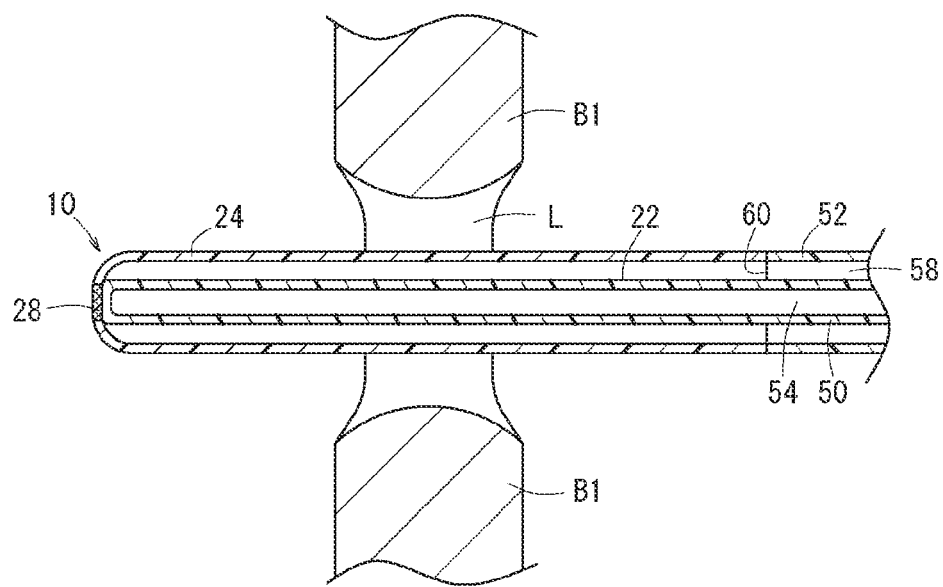
FIG. 8B is a sectional view taken along line VIIIB-VIIIB in FIG. 8A.

Thereafter, as illustrated in FIG. 8A, only the outer cylinder 82 (and the hub 84) is (are) moved rearward in a direction toward the proximal end so that the entire length of the spacer 10 is exposed inside the body (Step S13: outer cylinder rearward moving step). Here, as illustrated in FIG. 8B, the spacer 10 penetrates the interspinous ligament L at a position corresponding to the neck portion 20 (refer to FIG. 10B) of the outer balloon 24. In this state, a portion corresponding to the pair of bulged portions 18 of the outer balloon 24 is located on both sides of the spinous process B1.

If the spacer 10 is arranged in this state, the dilating fluid 70 is then introduced into the inner balloon 22 via the inner tube 50. In this manner, the inner balloon 22 dilates and the outer balloon 24 firstly dilates (Step S14: first dilating step). At this time, a dilating fluid supply source (not illustrated) is connected to the first port 66 of the hub 16, the dilating fluid supply source is operated, and the dilating fluid 70 is introduced into the inner balloon 22 via the inner tube 50.

In this first dilating step, if the dilating fluid 70 having lower viscosity than viscosity of the filling material 74 is introduced into the inner balloon 22, the entire body of the lumen 30 of the first cylindrical portion 32 configuring the inner balloon 22 is filled with the dilating fluid 70 substantially at the same time. Then, if the dilating fluid 70 is further introduced into the inner balloon 22, the respective first folded portions 34 dilate while rotating in a direction opposite to the bending direction thereof. At this time, the respective first folded portions 34 dilate after the entire body of the lumen 30 of the first cylindrical portion 32 can be filled with the dilating fluid 70. Accordingly, the entire body of the inner balloon 22 dilates substantially at the same time.

In addition, if the inner balloon 22 dilates, the inner balloon 22 presses the outer balloon 24 radially outward. Accordingly, the respective second folded portions 39 of the outer balloon 24 firstly dilate while rotating in a direction opposite to the bending direction thereof. At this time, the entire body of the inner balloon 22 dilates substantially at the same time. Accordingly, the entire body of the outer balloon 24 also firstly dilates substantially at the same time. In accordance with an exemplary embodiment, for example, when the outer balloon 24 is firstly dilates, any one of the distal side and the proximal side of the outer balloon 24 can be prevented from dilating earlier. Accordingly, the outer balloon 24 is prevented from being displaced when the outer balloon 24 firstly dilates.

In the present exemplary embodiment, the bending direction of the respective first folded portions 34 of the inner balloon 22 and the bending direction of the respective second folded portions 39 of the outer balloon 24 are the same as each other. Therefore, the rotating direction of the respective first folded portions 34 when the inner balloon 22 dilates and the rotation direction of the respective second folded portions 39 when the outer balloon 24 firstly dilates are the same as each other. Accordingly, the outer balloon 24 smoothly and firstly dilates in response to the dilation of the inner balloon 22.

The dilated inner balloon 22 has a cylindrical shape. In addition, the firstly dilated outer balloon 24 can have a cylindrical shape, which can be the same as the shape of the dilated inner balloon 22. In accordance with an exemplary embodiment, for example, the respective second folded portions 39 of the outer balloon 24 do not completely dilate when the outer balloon firstly dilates, but partially dilate. At this time, the outer balloon 24 is held by a reaction force acting from surrounding tissues because the outer balloon 24 widely presses the surrounding tissues due to the first dilating.

In accordance with an exemplary embodiment, when the outer diameter of the firstly dilated outer balloon 24 is set to be substantially the same as the outer diameter of the neck portion 20 of the outer balloon 24, a holding force of the firstly dilated outer balloon 24 can be increased.

In addition, the present embodiment employs the contrast agent as the dilating fluid 70. When performing the first dilating step, an operator checks a position and a dilate state of the inner balloon 22 (outer balloon 24) by using X-ray fluoroscope.

After the outer balloon 24 firstly dilates, a holding fluid supply source (not illustrated) is connected to the second port 68, the holding fluid supply source is operated, and the holding fluid 72 is introduced into a space between the inner balloon 22 and the outer balloon 24 (Step S15: holding fluid introducing step, refer to FIG. 9B). In accordance with an exemplary embodiment, for example, the holding fluid 72 is introduced into the space between the inner balloon 22 and the outer balloon 24 via the lumen 58 disposed between the inner tube 50 and the outer tube 52. In addition, the dilating fluid supply source is operated so as to absorb (pull out) the dilating fluid 70 which fills the inner balloon 22, via the inner tube 50 (Step S16: dilating fluid pulling-out step).

If the dilating fluid 70 is absorbed from the inner balloon 22, the inner balloon 22 deflates. However, at this time, the holding fluid 72 is introduced into the space between the inner balloon 22 and the outer balloon 24. Accordingly, the outer balloon 24 does not deflate, and maintains the firstly dilated state.

If the inner balloon 22 sufficiently deflates, the inner balloon 22 is removed from the outer balloon 24 (Step S17: removing step). For example, an operator grips and pulls the slide hub 64 toward the operator, thereby moving the slide hub 64 rearward to the proximal side of the hub body 62. In this manner, the inner balloon 22 connected to the slide hub 64 via the inner tube 50 is moved rearward to the proximal side of the outer balloon 24, and is removed therefrom.

In the removing step, in the present embodiment, the inner balloon 22 and the inner tube 50 are completely removed from the outer tube 52 and the hub body 62. In this case, when the outer balloon 24 is filled with the filling material 74 via the outer tube 52, the inner balloon 22 will not become resistive. Accordingly, the filling material 74 can be relatively smoothly introduced into the outer balloon 24. However, in the removing step, as long as the sufficiently deflated inner balloon 22 can be removed from the outer balloon 24, the inner balloon 22 may remain in the lumen 56 of the outer tube 52. In this case, a time required for the removing step can be shortened.

While this removing step is performed, the holding fluid 72 is continuously introduced into the outer balloon 24. Then, after the removing step is completed, the holding fluid supply source is operated so as to stop the introduction of the holding fluid 72 into the outer balloon 24, and the holding fluid supply source is detached from the second port 68. At this time, if a check valve is disposed in the second port 68, the holding fluid 72 is preferably prevented from flowing outward (the outer balloon 24 is caused to deflate). In this state, the pressure of the holding fluid 72 inside the outer balloon 24 can be moderately suppressed. Accordingly, the holding fluid 72 will not leak outward via the outflow portion 28.

After the removing step, the filling material 74 is introduced into the outer balloon 24, thereby causing the outer balloon 24 to secondly dilate (Step S18: second dilating step). At this time, a filling material supply source (not illustrated) is connected to the second port 68, the filling material supply source is operated, and the filling material 74 is introduced into the outer balloon 24 via the lumen 56 (or the lumen 58) of the outer tube 52. If the filling material 74 is introduced into the outer balloon 24, the pressure of the holding fluid 72 inside the outer balloon 24 increases, and the holding fluid 72 having predetermined pressure or greater is caused to flow outward (into the living body) from the outer balloon 24 via the outflow portion 28. In the present embodiment, since air is used as the holding fluid 72, the air will not adversely affect the patient P even when the holding fluid 72 flows into the living body (refer to FIG. 10A).

In this second dilating step, the respective second folded portions 39 of the outer balloon 24 dilate to some extent during the first dilating. Accordingly, the entire body of the outer balloon 24 secondly dilates substantially at the same time. The secondly dilated outer balloon 24 shows a shape in which the pair of bulged portions 18 is connected to each other via the neck portion 20. In this state, the neck portion 20 penetrates the interspinous ligament L between the spinous processes B1, and the interspinous ligament L is located between the pair of spinous processes 18 on both sides thereof. In this manner, the neck portion 20 expands a space between the spinous processes B1, and the spacer 10 is brought into a state where the spacer 10 can be prevented from slipping out from the interspinous ligament L between the spinous processes B1 (refer to FIG. 10B).

Figure 11A:
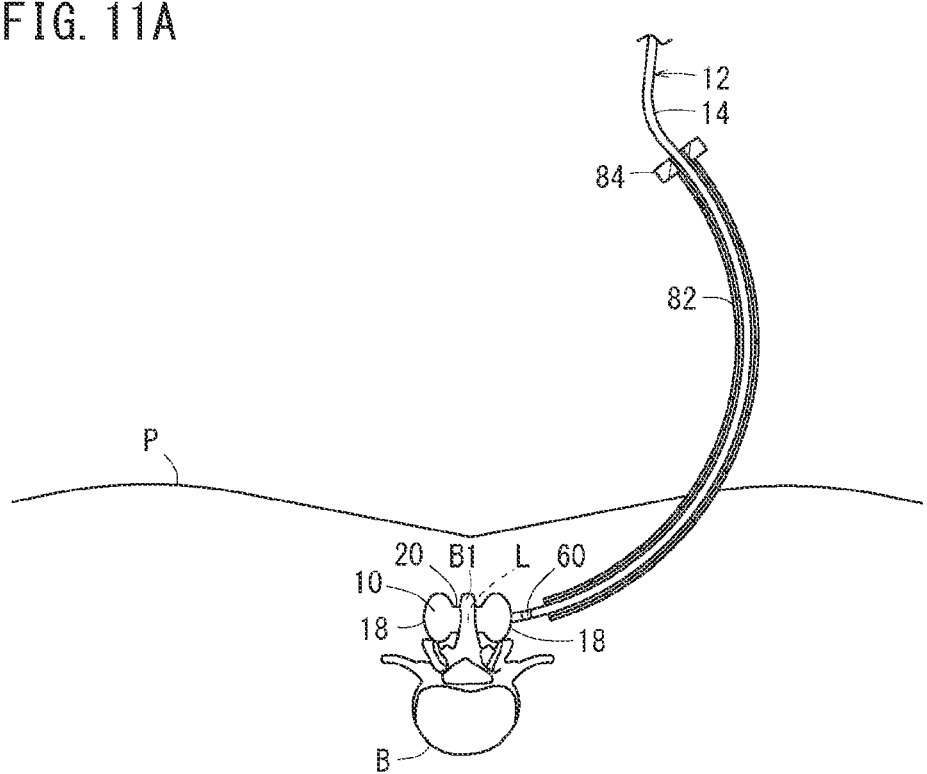
FIG. 11A is a view for describing a state where the spacer dilates at a desired position between spinous processes.
Figure 11B:
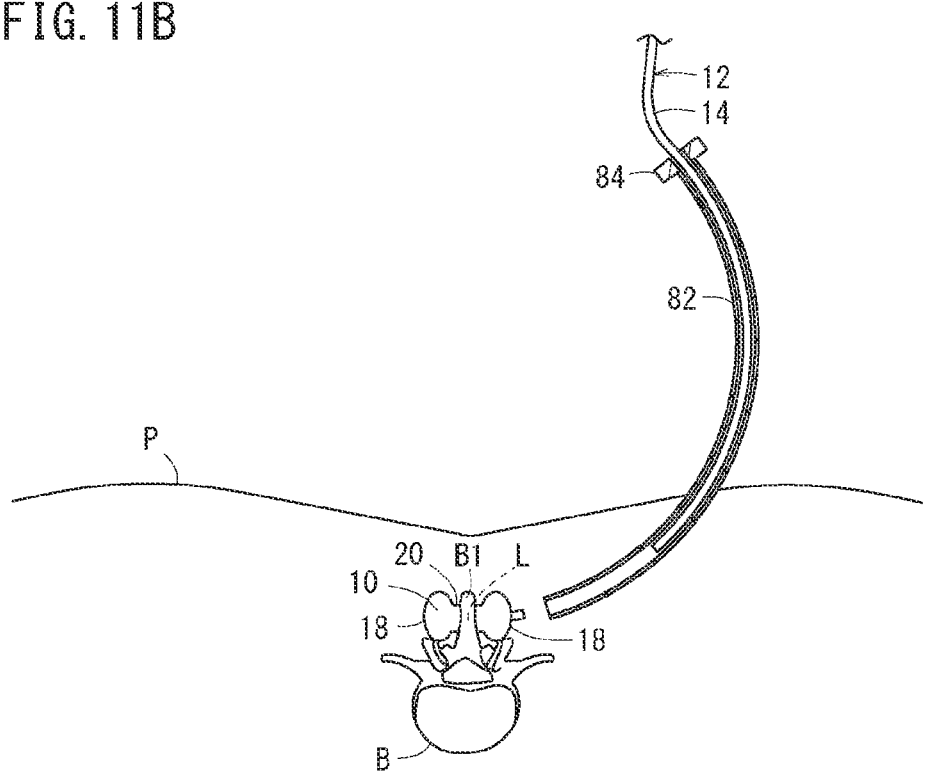
FIG. 11B is a view for describing a separating step according to the surgical method for spacer indwelling.

If the outer balloon 24 sufficiently dilates, the outer balloon 24 and the outer tube 52 can be separated from each other, as illustrated in FIG. 11B (Step S19: separating step). When the connection structure 60 between the outer balloon 24 and the outer tube 52 is a screw structure, if the outer tube 52 is rotated around its axis, the outer balloon 24 inserted into the interspinous ligament L between the spinous processes B1 adjacent to each other is not rotated. Only the outer tube 52 is rotated, thereby causing the outer balloon 24 and the outer tube 52 to be unscrewed, which can separate the outer balloon 24 and the outer tube 52 from each other.

If the filling material 74 is a material which is fluidic when injected and is cured after injected, it can be preferable to separate the outer balloon 24 and the outer tube 52 from each other, after the filling material 74 is cured. If the filling material 74 is a material, which maintains a fluidic state even after injected, it can be preferable to dispose a backflow preventing structure (check valve) in an inlet of the outer balloon 24.

If the outer balloon 24 and the outer tube 52 are separated from each other, the tube 14 is removed from the outer cylinder 82, and the outer cylinder 82 is completely removed from the patient P (Step S20: outer cylinder removing step). In this manner, the spacer 10 is brought into a state of indwelling between the spinous processes B1, and a surgery according to the present exemplary embodiment is completely performed.

As describe above, according to the present exemplary embodiment, if the dilating fluid 70 having the lower viscosity than the viscosity of the filling material 74 is introduced into the inner balloon 22, the entire body of the lumen 30 of the first cylindrical portion 32 configuring the inner balloon 22 is filled with the dilating fluid 70 substantially at the same time. Then, the entire body of the inner balloon 22 dilates substantially at the same time. Accordingly, in response to the dilation of the inner balloon 22, the entire body of the outer balloon 24 dilates substantially at the same time, which can help prevents any one of the distal side and the proximal side of the outer balloon 24 from firstly dilating earlier. Therefore, the outer balloon 24 can be prevented from being displaced when the outer balloon 24 firstly dilates. At this stage, the outer balloon 24 dilates (is deployed) while a portion of the respective second folded portions 39 of the outer balloon 24 presses the surrounding tissues.

In addition, the inner balloon 22 deflates by absorbing (pulling out) the dilating fluid 70, which helps enable the inner balloon 22 to be removed from the firstly dilated outer balloon 24. At this time, the firstly dilated outer balloon 24 will not be folded again. Therefore, if the filling material is introduced into the firstly dilated outer balloon 24, the entire body of the outer balloon 24 secondly dilates substantially at the same time, which can help prevent any one of the distal side and the proximal side of the outer balloon 24 from secondly dilating earlier. Accordingly, the spacer 10 can be prevented from being displaced when the spacer 10 is indwelled between bones.

In the present exemplary embodiment, when the inner balloon 22 is deflated by pulling out the dilating fluid 70, the holding fluid 72 for maintaining a first dilated state of the outer balloon 24 is introduced into the space between the outer balloon 24 and the inner balloon 22, which helps enable the deflated inner balloon 22 to be removed relatively easily from the outer balloon 24. In addition, during the removal, the outer balloon 24 maintains the firstly dilated state. Accordingly, a reaction force acting from the surrounding tissues holds the outer balloon 24, which can help prevent the outer balloon 24 from being displaced when the outer balloon 24 secondly dilates. Furthermore, since the outflow portion 28 is provided, the filling material 74 can be introduced relatively easily into the outer balloon 24, which maintains the firstly dilated state.

In this case, the filling material 74 is introduced from the proximal end of the outer balloon 24, and the outflow portion 28 is disposed in the distal end of the outer balloon 24. In this manner, the filling material 74 introduced from the proximal end of the outer balloon 24 can progressively presses the holding fluid 72 against the outflow portion 28 disposed in the distal end of the outer balloon 24, which can help enable the holding fluid 72 to be smoothly pulled out of the outer balloon 24.

In addition, the outflow portion 28 allows the circulation of the holding fluid 72 having predetermined pressure or greater, and blocks the circulation of the filling material 74 and the holding fluid 72 having lower pressure than the predetermined pressure. Therefore, before the filling material 74 is introduced into the outer balloon 24, the holding fluid 72 can be prevented from flowing outward from the outer balloon 24 via the outflow portion 28, which helps enable the holding fluid 72 to preferably maintain the firstly dilated state of the outer balloon 24. In addition, when the pressure of the holding fluid 72 increases since the filling material 74 is introduced into the outer balloon 24, the holding fluid 72 can reliably flow out from the outer balloon 24 via the outflow portion 28. In this case, the filling material 74 will not leak out from the outer balloon 24.

According to the present exemplary embodiment, the respective first folded portions 34 can be bent in the same circumferential direction in a state where the inner balloon 22 deflates. Accordingly, the respective first folded portions 34 dilate while rotating in the direction opposite to the bending direction thereof. In addition, the respective second folded portions 39 can be bent in the same circumferential direction in a state where the outer balloon 24 deflates. Accordingly, the respective second folded portions 39 dilate while rotating in the direction opposite to the bending direction thereof. Then, the bending direction of the respective first folded portions 34 and the bending direction of the respective second folded portions 39 are the same as each other. Then, the rotating direction of the respective first folded portions 34 when the inner balloon 22 dilates and the rotating direction of the respective second folded portions 39 when the outer balloon 24 firstly dilates become the same as each other. In this manner, compared to a case where the bending direction of the respective first folded portions 34 and the bending direction of the respective second folded portions 39 are opposite to each other, the outer balloon 24 can smoothly and firstly dilate.

According to the present exemplary embodiment, in a state where the spacer 10 deflates, the respective first folded portions 34 of the inner balloon 22 are arranged in the lumen 36 in the second cylindrical portion 38 of the outer balloon 24 without being interposed between the respective second folded portions 39 of the outer balloon 24. Therefore, when the inner balloon 22 is caused to dilate, the respective first folded portions 34 can be relatively rotated with respect to the outer balloon 24. In this manner, compared to a case where the respective first folded portions 34 are interposed between the respective second folded portions 39, a configuration can be adopted in which a rotational force of the respective first folded portions 34 when the inner balloon 22 dilates is less likely to be transmitted to the outer balloon 24. Accordingly, the outer balloon 24 can be prevented from being displaced by the outer balloon 24 being rotated when the outer balloon 24 firstly dilates.

In addition, in a case of the present embodiment, the number of the first folded portions 34 and the number of the second folded portions 39 are the same as each other, and the circumferential position of the multiple first folded portions 34 and the circumferential position of the multiple second folded portions 39 correspond to each other. Therefore, the respective first folded portions 34 which are dilated by the dilating fluid 70 can be dilated by contacting with the respective second folded portions 39. In this manner, the outer balloon 24 can smoothly and firstly dilate.

According to the present exemplary embodiment, the inner balloon 22 in a dilated state has a cylindrical shape. The outer balloon 24 in a secondly dilated state has a shape, which has the neck portion 20 and the bulged portions 18 respectively disposed on both sides of the neck portion 20. Therefore, the shape of the outer balloon 24 in a firstly dilated state can employ the cylindrical shape, which is the same as the shape of the inner balloon 22 in a dilated state. In this manner, compared to a case where the shape when the inner balloon 22 dilates is set to be the shape when the outer balloon 24 dilates (shape including the neck portion 20 and the pair of bulged portions 18), an amount of rotation around the axis of the outer balloon 24 can be reduced. Accordingly, it is possible to more efficiently prevent the outer balloon 24 can efficiently be prevented from being displaced when the outer balloon 24 firstly dilates. In addition, the pair of bulged portions 18 is formed in a secondly dilated state of the outer balloon 24. Therefore, the outer balloon 24 which secondly dilates can be prevented from slipping out from a space between the spinous processes B1.

The present exemplary embodiment is not limited to the above-described configurations and methods. In accordance with an exemplary embodiment, for example, the spacer 10 may not have the outflow portion 28. In this case, in the above-described surgical method for spacer indwelling, the holding fluid introducing step (Step S15) is not performed, and steps other than Step S15 are performed.

When the holding fluid introducing step is not performed, if the dilating fluid 70 is absorbed from (pulled out of) the inner balloon 22 in the dilating fluid pulling-out step (Step S16), in response to the deflation of the inner balloon 22, the outer balloon 24 in a firstly dilated state deflates after receiving external pressure generated by the surrounding tissues such as the tissues of the spinous processes, interspinous ligament, and the like. However, the respective second folded portions 39 have already partially dilated (been deployed) during the first dilating. Accordingly, a deflated amount of the outer balloon 24 shows a slight amount. Therefore, in the removing step (Step S17), the inner balloon 22 can be removed from the outer balloon 24.

In addition, if the filling material 74 is introduced into the outer balloon 24 in the second dilating step (Step S19), substantially the entire body of the outer balloon 24 secondly dilates at the same time. Accordingly, the spacer 10 is prevented from being displaced when the spacer 10 is indwelled between the spinous processes B1.

Figure 12A:
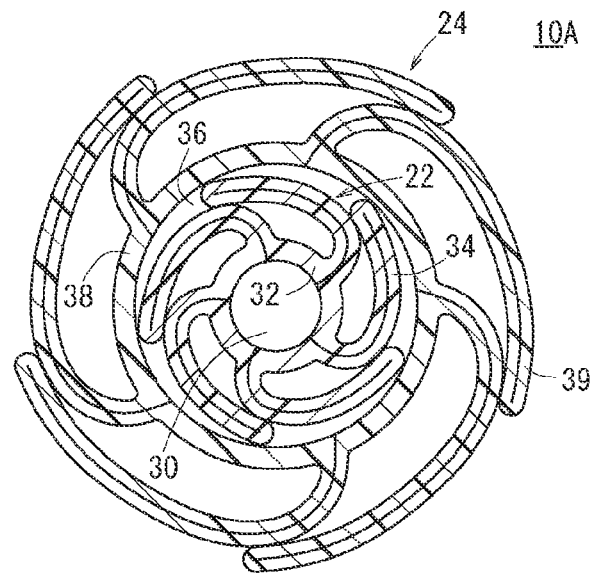
FIG. 12A is a horizontal sectional view illustrating another configuration example of the spacer.

The spacer 10 is not limited to the above-described configuration. For example, a spacer 10A as illustrated in FIG. 12A may be employed. Compared to the above-described spacer 10, this spacer 10A is different in that the bending direction of the respective first folded portions 34 in the inner balloon 22 and the bending direction of the respective second folded portions 39 in the outer balloon 24 are opposite to each other. This spacer 10A can be obtained by bending the respective second pleated portions 46 in the direction opposite to the bending direction of the respective first pleated portions 42 in second bending step (Step S4 in FIG. 3).

According to the spacer 10A, the rotating direction of the respective first folded portions 34 when the inner balloon 22 dilates and the rotating direction of the respective second folded portions 39 when the outer balloon 24 firstly dilates are opposite to each other. In this manner, compared to a case where the bending direction of the respective first folded portions 34 and the bending direction of the respective second folded portions 39 are set to be the same as each other, it is possible to prevent the outer balloon 24 from rotating around its axis when the outer balloon 24 firstly dilates. Accordingly, the outer balloon 24 can be prevented from being displaced when the outer balloon 24 first dilates.

Figure 12B:
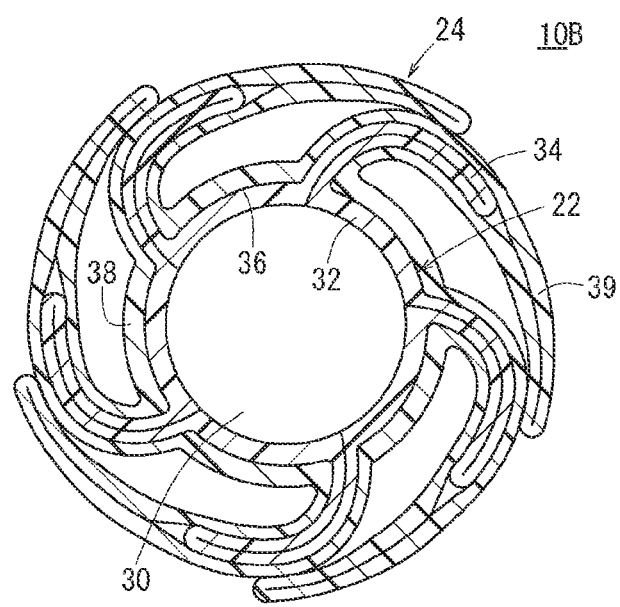
FIG. 12B is a horizontal sectional view illustrating still another configuration example of the spacer.

Furthermore, the present exemplary embodiment may employ a spacer 10B illustrated in FIG. 12B, for example. Compared to the above-described spacer 10, this spacer 10B is different in that the respective first folded portions 34 of the inner balloon 22 are interposed between the respective second folded portions 39 of the outer balloon 24.

Figure 13:
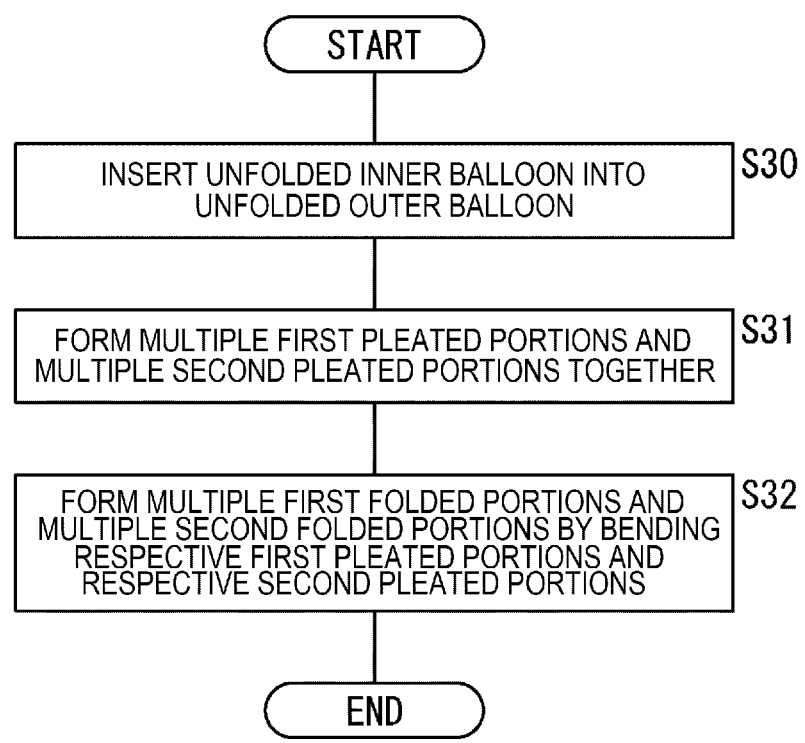
FIG. 13 is a flowchart illustrating a procedure of the manufacturing method of the spacer illustrated in FIG. 12B.
Figure 14A:
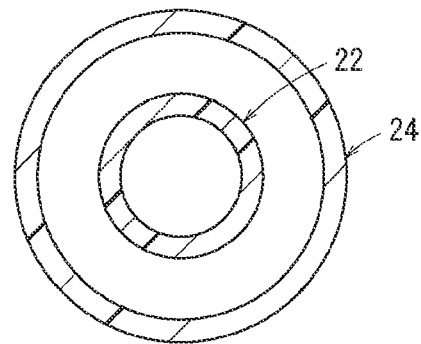
FIG. 14A is a first view for describing the manufacturing method of the spacer illustrated in FIG. 12B.

This spacer 10B can be manufactured as follows. In accordance with an exemplary embodiment, for example, the inner balloon 22 having an unfolded bag shape is first inserted into the outer balloon 24 having an unfolded bag shape (Step S30 in FIG. 13, refer to FIG. 14A).

Figure 14B:
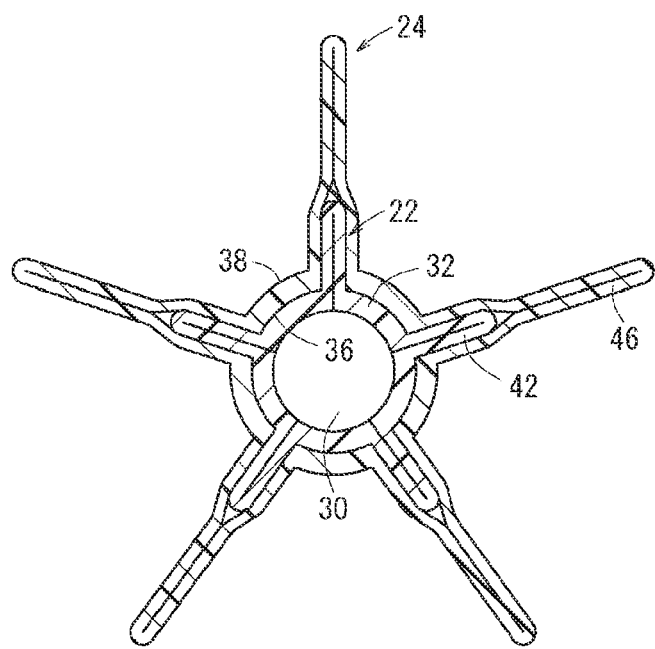
FIG. 14B is a second view for describing the manufacturing method of the spacer illustrated in FIG. 12B.

Then, the inner balloon 22 and the outer balloon 24 are folded together so that at multiple locations in the circumferential direction of the inner balloon 22 and the outer balloon 24, inner surfaces at the respective locations come into contact with each other. In accordance with an exemplary embodiment, for example, the first cylindrical portion 32 is formed at the center of the inner balloon 22, and the first pleated portion 42 radially protruding is formed at multiple locations in the circumferential direction. The second cylindrical portion 38 is formed around the center of the outer balloon 24, and the second pleated portion 46 radially protruding is formed at multiple locations in the circumferential direction. (Step S31, refer to FIG. 14B). In accordance with an exemplary embodiment, for example, the respective first pleated portions 42 and the respective second pleated portions 46 can be formed together. In this state, the respective first pleated portions 42 can be interposed between the respective second pleated portions 46.

Thereafter, the respective first pleated portions 42 and the respective second pleated portions 46 are bent together in the same circumferential direction, and are brought into a state of being folded in the circumferential direction as illustrated in FIG. 12B (Step S32). In this manner, the inner balloon 22 including the first cylindrical portion 32 and the multiple first folded portions 34 and the outer balloon 24 including the second cylindrical portion 38 and the second folded portions 39 can be obtained. At this stage, the spacer 10B is completely manufactured. Even in a case of employing this spacer 10B, the spacer 10B is prevented from being displaced when the spacer 10B is indwelled between the spinous processes B1.

Figure 15A:
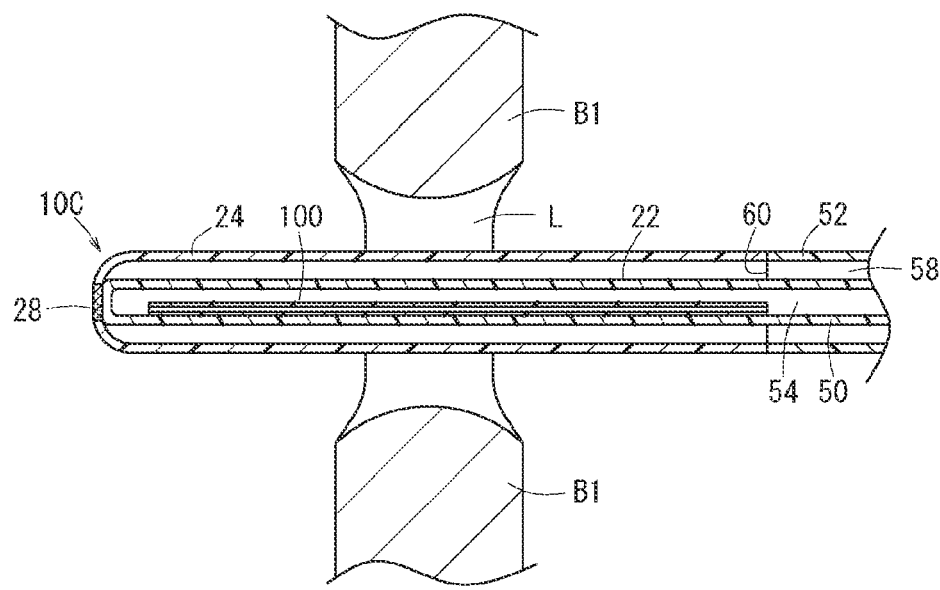
FIG. 15A is a horizontal sectional view illustrating still another configuration example of the spacer.

Furthermore, the present exemplary embodiment may employ a spacer 10C illustrated in FIG. 15A. Compared to the above-described spacer 10, this spacer 10C is different in that a bypass passage 100 is disposed inside the inner balloon 22. The bypass passage 100 introduces a portion of the dilating fluid 70 inside the proximal portion of the inner balloon 22 into the distal side of the inner balloon 22.

In the illustrated example, the bypass passage 100 is configured to have a tubular shape, and the proximal portion thereof is fixed to the proximal portion of the inner balloon 22. However, as long as the bypass passage 100 has a configuration in which a portion of the dilating fluid 70 inside the proximal portion of the inner balloon 22 can be introduced into the distal side of the inner balloon 22, the embodiment can employ any desired configuration without being limited to the illustrated example. In accordance with an exemplary embodiment, for example, the bypass passage 100 may employ a configuration which is the same as the configuration disclosed in the specification and the drawings of Japanese Patent Application No. 2012-215524.

Figure 15B:
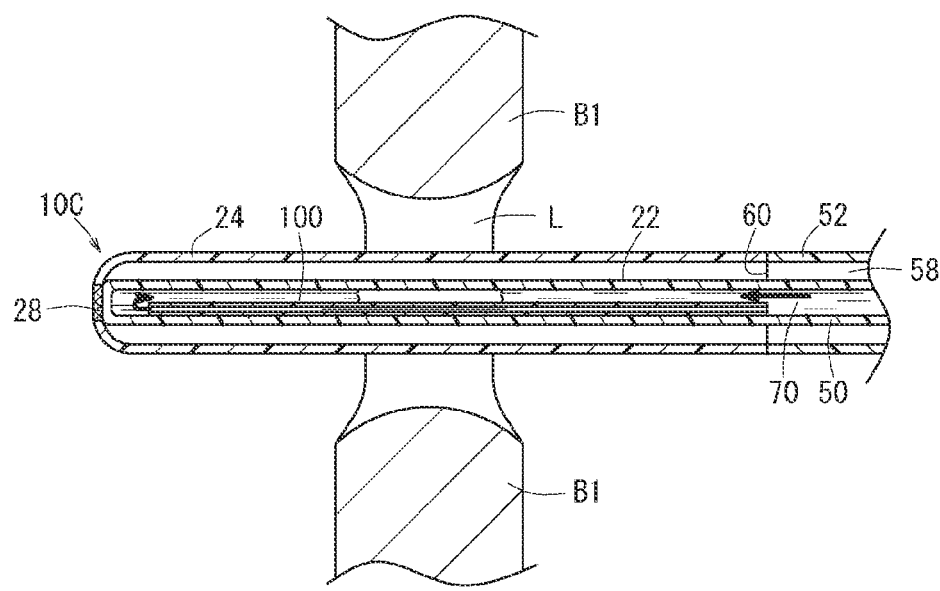
FIG. 15B is a view for describing a state where a dilating fluid starts to be introduced into an inner balloon configuring the spacer.
Figure 16:
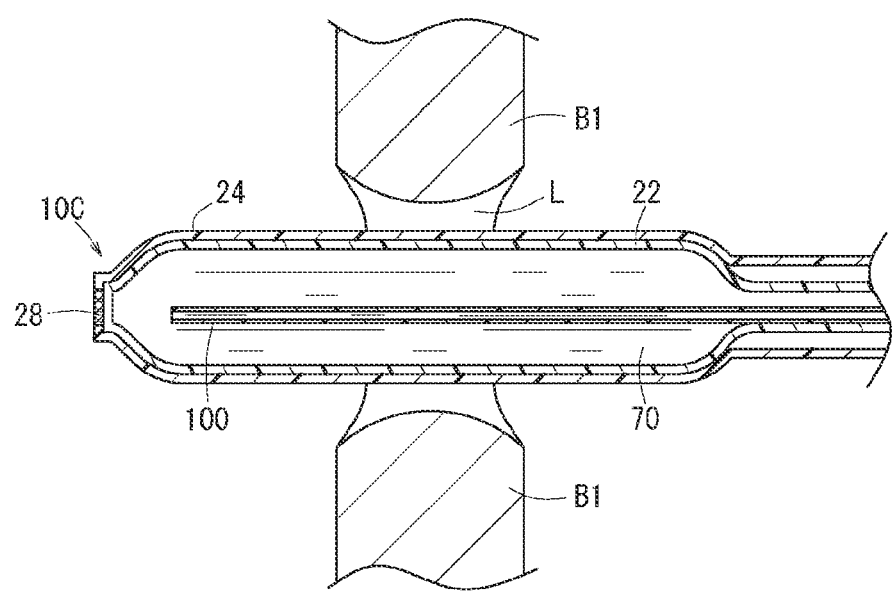
FIG. 16 is a view for describing a firstly dilated state of the spacer illustrated in FIG. 15B.

As illustrated in FIG. 15B, if the dilating fluid 70 is injected to the inner balloon 22 in the spacer 10C, the dilating fluid 70 is introduced into the proximal side of the inner balloon 22 via the outer side of the bypass passage 100, and the dilating fluid 70 is introduced into the distal side of the inner balloon 22 via the bypass passage 100. In this manner, it is possible to match the timing for filling the proximal side of the inner balloon 22 with the dilating fluid 70 and the timing for filling the distal side of the inner balloon 22 with the dilating fluid 70 can be matched so as to be much closer to each other. Accordingly, any one of the distal side and the proximal side of the outer balloon 24 can be prevented from first dilating earlier. Therefore, the outer balloon 24 can be prevented from being displaced when the outer balloon 24 firstly dilates (refer to FIG. 16).

In addition, the respective spacers 10, 10A, 10B, and 10C may have outer balloons 24a to 24f in a dilated state respectively having shapes illustrated in FIGS. 17A to 17F. Furthermore, the outflow portion 28 may be disposed in substantially the center or on the proximal side in the axial direction of the outer balloon 24. Even in this case, the holding fluid 72 inside the outer balloon 24 can flow outward.

Hitherto, the present invention has been described with reference to the preferred embodiments. However, without being limited to the above-described embodiments, the present invention can be improved and modified in various ways within the scope not departing from the gist of the present invention, as a matter of course.

The detailed description above describes a spacer, an implant assembly including the same, a manufacturing method of a spacer, and a surgical method for spacer indwelling. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A spacer configured to indwell between bones so as to expand a space between the bones, the spacer comprising:
    an outer balloon that is folded so as to be dilatable;
    an inner balloon that is folded so as to be dilatable, and that is removably inserted into the outer balloon, wherein the inner balloon is configured to dilate in response to introduction of a dilating fluid having a lower viscosity than a viscosity of a filling material introduced into the outer balloon, the inner balloon in a dilated state having a cylindrical shape; and
    wherein the outer balloon is configured to dilate in response to the dilation of the inner balloon, the outer balloon in a fully dilated state having a neck portion and bulged portions disposed on both sides of the neck portion.

2. The spacer according to claim 1, wherein in a deflated state of the inner balloon, multiple first folded portions which are bent in a same circumferential direction are formed at multiple locations in a circumferential direction about a longitudinal axis of the inner balloon;
    in a deflated state of the outer balloon, multiple second folded portions which are bent in a same circumferential direction are formed at multiple locations in a circumferential direction about a longitudinal axis of outer balloon; and
    a bending direction of the multiple first folded portions and a bending direction of the multiple second folded portions are same as each other.

3. The spacer according to claim 2, wherein in the deflated state of the outer balloon, a lumen in which the deflated inner balloon is to be arranged is formed in a central portion of the outer balloon; and
    the multiple first folded portions are arranged in the lumen without being interposed between the multiple second folded portions.

4. The spacer according to claim 2, comprising:
    a position of a base of each of the multiple first folded portions in the circumferential direction and a position of a base of each of the multiple second folded portions in the circumferential direction correspond to each other.

5. The spacer according to claim 2, wherein the multiple first folded portions are arranged at equal intervals in the circumferential direction about the axis of inner balloon; and
    the multiple second folded portions being arranged at equal intervals in the circumferential direction about the axis of outer balloon.

6. The spacer according to claim 1, wherein in a deflated state of the inner balloon, multiple first folded portions which are bent in a same circumferential direction are formed at multiple locations in a circumferential direction about a longitudinal axis of the inner balloon;
    in a deflated state of the outer balloon, multiple second folded portions which are bent in a same circumferential direction are formed at multiple locations in a circumferential direction about a longitudinal axis of the outer balloon; and
    a bending direction of the multiple first folded portions and a bending direction of the multiple second folded portions are opposite to each other.

7. The spacer according to claim 1, wherein the outer balloon in a partially dilated state has a cylindrical shape, the cylindrical shape of the outer balloon in the partially inflated state being a same shape as the cylindrical shape of the inner balloon in the dilated state.

8. The spacer according to claim 7, wherein the partially dilated state of the outer balloon occurs simultaneously with the dilated state of the inner balloon.

9. The spacer according to claim 1, wherein the outer balloon in the fully inflated state has a dumbbell shape in a cross-sectional along the longitudinal axis.

10. An assembly comprising:
    a spacer configured to indwell between bones so as to expand a space between the bones, the spacer including an outer balloon that is folded so as to be dilatable and an inner balloon that is folded so as to be dilatable, and that is removably inserted into the outer balloon, wherein the inner balloon is configured to dilate in response to introduction of a dilating fluid having a lower viscosity than a viscosity of a filling material introduced into the outer balloon, and wherein the outer balloon is configured to dilate in response to the dilation of the inner balloon;
    a holding fluid for maintaining a dilated state of the outer balloon when the inner balloon is deflated by removing the dilating fluid from the inner balloon, the holding fluid being introduced into a portion between the inner balloon and the outer balloon; and an outflow portion configured to cause the holding fluid inside the outer balloon to flow outward, in response to the filling material being introduced into the outer balloon.

11. The spacer according to claim 10, wherein the filling material is introduced from a proximal end of the outer balloon, and the outflow portion is disposed in a distal end of the outer balloon.

12. The spacer according to claim 11, wherein the outflow portion allows circulation of the holding fluid having a predetermined pressure or greater, and blocks the circulation of the filling material and the holding fluid having a pressure which is smaller than the predetermined pressure.

13. An implant assembly comprising:
   a spacer configured to indwell between bones as an implant for expanding a space between the bones, the spacer comprising:
      an outer balloon that is folded so as to be dilatable;
      an inner balloon that is folded so as to be dilatable, and that is removably inserted into the outer balloon, wherein the inner balloon is configured to dilate in response to introduction of a dilating fluid which has a lower viscosity than a viscosity of a filling material introduced into the outer balloon, the inner balloon in a dilated state having a cylindrical shape; and
      the outer balloon configured to dilate in response to the dilation of the inner balloon, the outer balloon in a fully dilated state having a neck portion and bulged portions disposed on both sides of the neck portion;
   a catheter tube that is detachably connected to a proximal end of the spacer; and
   a hub that is connected to a proximal end of the catheter tube.

14. The implant assembly according to claim 13, wherein in a deflated state of the inner balloon, multiple first folded portions which are bent in a same circumferential direction are formed at multiple locations in a circumferential direction about a longitudinal axis of the inner balloon;
   in a deflated state of the outer balloon, multiple second folded portions which are bent in a same circumferential direction are formed at multiple locations in a circumferential direction about a longitudinal axis of the outer balloon; and
   a bending direction of the multiple first folded portions and a bending direction of the multiple second folded portions are same as each other.

15. The implant assembly according to claim 14, wherein in the deflated state of the outer balloon, a lumen in which the deflated inner balloon is to be arranged is formed in a central portion of the outer balloon; and
   the multiple first folded portions are arranged in the lumen without being interposed between the multiple second folded portions.

16. The implant assembly according to claim 14, comprising:
   a position of a base of each of the multiple first folded portions in the circumferential direction and a position of a base of each of the multiple second folded portions in the circumferential direction correspond to each other.

17. The implant assembly according to claim 13, wherein in a deflated state of the inner balloon, multiple first folded portions which are bent in a same circumferential direction are formed at multiple locations in a circumferential direction about a longitudinal axis of the inner balloon;
   in a deflated state of the outer balloon, multiple second folded portions which are bent in a same circumferential direction are formed at multiple locations in a circumferential direction about a longitudinal axis of the outer balloon; and
   a bending direction of the multiple first folded portions and a bending direction of the multiple second folded portions are opposite to each other.

18. A surgical method for spacer indwelling in which a spacer indwells between bones so as to expand a space between the bones, the method comprising:
   inserting the spacer including an outer balloon that is folded so as to be dilatable and an inner balloon that is folded so as to be dilatable and that is inserted into the outer balloon, into the space between the bones;
   dilating the inner balloon by introducing a dilating fluid having lower viscosity than viscosity of a filling material into the inner balloon, the inner balloon in a dilated state having a cylindrical shape, and partially dilating the outer balloon in response to the dilation of the inner balloon;
   deflating the inner balloon by removing the dilating fluid from the inside of the inner balloon;
   removing the deflated inner balloon from the outer balloon; and
   dilating the outer balloon by introducing additional filling material into the outer balloon, and wherein the outer balloon in a fully dilated state has a neck portion and bulged portions disposed on both sides of the neck portion.

19. The surgical method for spacer indwelling according to claim 18, comprising:
   maintaining a dilated state of the outer balloon by introducing a holding fluid into a portion between the inner balloon and the outer balloon during the removal of the dilating fluid from the inside of the balloon and the removing of the deflated inner balloon from the outer balloon; and
   causing the holding fluid inside the outer balloon to flow outward via an outflow portion, in response to the filling material being introduced into the outer balloon.

* * * * *